United States Patent [19]
Jones

[11] Patent Number: 5,215,980
[45] Date of Patent: Jun. 1, 1993

[54] 10-AZA-9-DEOXO-11-DEOXY-ERYTHROMYCIN A AND DERIVATIVES THEREOF

[75] Inventor: Anthony B. Jones, Scotch Plains, N.J.

[73] Assignee: Merck & Co., Inc., Rahway, N.J.

[21] Appl. No.: 822,497

[22] Filed: Jan. 17, 1992

[51] Int. Cl.$^5$ .................. A61K 31/33; C07D 413/14
[52] U.S. Cl. .................................. 514/183; 540/480; 540/482; 540/454
[58] Field of Search .................. 540/454, 480, 482; 514/183

[56] References Cited

U.S. PATENT DOCUMENTS

| | | | |
|---|---|---|---|
| 4,328,334 | 5/1982 | Kobrehel et al. | 536/7.4 |
| 4,464,527 | 8/1987 | Bright et al. | 536/7.4 |
| 4,465,674 | 8/1985 | Bright et al. | 424/180 |
| 4,492,688 | 1/1985 | Bright et al. | 424/180 |
| 4,512,982 | 4/1985 | Hanske et al. | 514/29 |
| 4,517,359 | 5/1985 | Kobrehel et al. | 536/7.4 |
| 4,518,590 | 5/1985 | Hauske et al. | 514/29 |
| 4,886,792 | 12/1989 | Djokic | 514/183 |
| 4,957,905 | 9/1990 | Hunt et al. | 514/29 |
| 5,526,889 | 6/1985 | Bright et al. | 514/29 |

FOREIGN PATENT DOCUMENTS

| | | |
|---|---|---|
| 0101186 | 2/1984 | European Pat. Off. |
| 0109253 | 5/1984 | European Pat. Off. |
| 0136831 | 4/1985 | European Pat. Off. |
| 0259789 | 3/1986 | European Pat. Off. |
| 0283055 | 9/1988 | European Pat. Off. |
| 0307128 | 5/1989 | European Pat. Off. |
| 0298650 | 11/1989 | European Pat. Off. |

OTHER PUBLICATIONS

Fernandes, P., *The Macrolide Revival*, The Antimicrobic Newsleter, vol. 4, No. 4, pp. 25-36, Apr., 1987, U.S.A.
Djokic, et al., Erythromycin Series Part 13: Synthesis and Structure Elucidation of 10-Dihydro-10-Dihydro-10-deoxo-11-methyl-11-azaerythromycin A. J. Chem. Research(s), 1988, pp. 152-153, U.K.
Bright, et al., Synthesis, In Vitro and In Vivo Activity of Novel 9-Oeoxo-9a-Aza-9a-Homoerythromycin A Derivatives; A New Class of Macrolide Antibiotics, the azalides, J. of Antibio. vol. 41, No. 8, Aug. 1988, pp. 1029-1047 USA.

*Primary Examiner*—Mukund J. Shah
*Assistant Examiner*—Y. N. Gupta
*Attorney, Agent, or Firm*—Frank P. Grassler; Richard C. Billups; Raymond M. Speer

[57] ABSTRACT

Compounds of the formula:

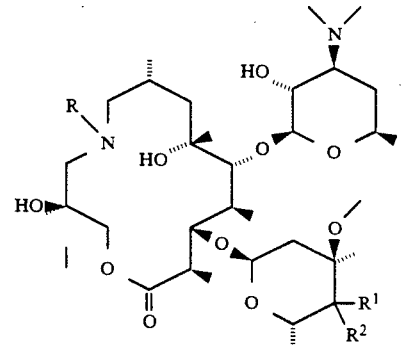

where R is hydrogen, $C_1$–$C_{10}$ alkylcarbonyl, or $C_1$–$C_{10}$ alkyl which can be substituted by amino or cyano, $R^1$ and $R^2$ are independently hydrogen, hydroxyl or amino, and the pharmaceutically aceptable salts and esters thereof. Pharmaceutical compositions and methods of their use are also provided for.

8 Claims, No Drawings

10-AZA-9-DEOXO-11-DEOXY-ERYTHROMYCIN A AND DERIVATIVES THEREOF

BACKGROUND OF THE INVENTION

The present invention relates to a novel group of chemical compounds having antibacterial activity, which are useful in the therapy of bacterial infections in mammals. More specifically, the invention relates to derivatives of the well-known macrolide antibiotic, erythromycin A, the compound of the structure:

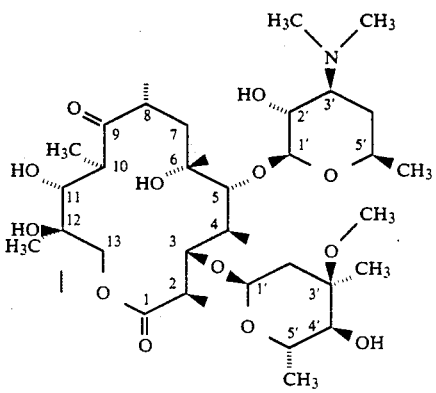

The erythromycin derivatives of the invention relate to the compounds of the structure:

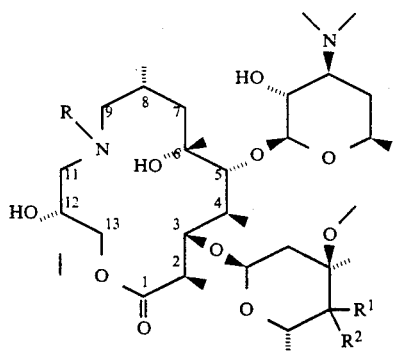

and derivatives thereof, which form a novel class of 14-membered azalides characterized in that the heterocyclic nitrogen atom is situated at the 10 position.

The present invention also provides for novel pharmaceutical compositions and methods of their use as antibiotic agents.

SUMMARY OF THE INVENTION

The present invention relates to novel compounds that are azalides of the following structure:

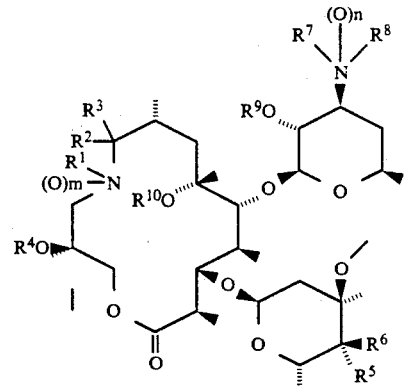

and the pharmaceutically acceptable salts, esters and metal complexes thereof, wherein $R^1$ is hydrogen, hydroxy, carbonyl, $C_1-C_{10}$ alkoxycarbonyl, arylsulfonate, $C_1-C_{10}$ alkylsulfonate, unsubstituted or substituted $C_1-C_{10}$ alkyl, or unsubstituted or substituted $C_1-C_{10}$ alkylcarbonyl, wherein said substituents are halogen, cyano, aryl, 5 or 6 membered heterocyclic rings having 1 heteroatom where said heteroatom is O or N, indole, isoindole, $C_1-C_{10}$ alkoxycarbonyl, $C_1-C_{10}$ alkoxy, hydroxy, mercapto, $C_1-C_{10}$ alkylthio, amino, mono- or di- $C_1-C_{10}$ alkyl amino or $C_1-C_{10}$ alkylcarbonylamino;

$R^2$ and $R^3$ are hydrogen;

$R^2$ and $R^3$ together are oxo or thiono;

$R^4$ is hydrogen, $C_1-C_{10}$ alkyl or, $C_1-C_{10}$ alkylcarbonyl;

$R^1$ and $R^4$ together are $C_1-C_3$ alkylidene which can be substituted by oxo;

$R^5$ and $R^6$ independently are hydrogen, hydroxy, $C_{1-10}$ alkoxy, $C_{1-10}$ alkylcarbonyloxy or $NHR^{11}$ wherein $R^{11}$ is hydrogen, hydroxy, carbonyl, $C_1-C_{10}$ alkoxycarbonyl, arylsulfonyl, $C_1-C_{10}$ alkylsulfonyl, unsubstituted or substituted $C_1-C_{10}$ alkyl, or unsubstituted or substituted $C_1-C_{10}$ alkylcarbonyl, wherein said substituents are halogen, cyano, aryl, 5 and 6 membered heterocyclic rings having 1 heteroatom where said heteroatom is N or O, indole, isoindole, $C_1-C_{10}$ alkoxycarbonyl, $C_1-C_{10}$ alkoxy, hydroxy, mercapto, $C_1-C_{10}$ alkylthio, amino, mono- or di- $C_1-C_{10}$ alkyl amino or $C_1-C_{10}$ alkylcarbonylamino;

$R^5$ and $R^6$ together are oxo or oximino;

$R^7$ and $R^8$ are independently hydrogen, $C_1-C_{10}$ alkyl, $C_1-C_{10}$ alkylcarbonyl, or arylsulfonyl;

$R^9$ is hydrogen or $C_1-C_{10}$ alkylcarbonyl;

$R^{10}$ is hydrogen or $C_1-C_{10}$ alkyl;

$R^1$ and $R^{10}$ together are $C_1-C_3$ alkylidene which can be substituted by oxo;

m and n are independently integers of from 0 to one; and said metal complex is taken from the group consisting of
copper,
zinc,
cobalt,
nickel or
cadmium.

A most preferred group of compounds is that of the following formula

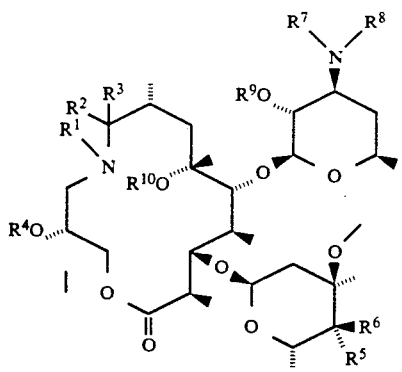

and the pharmaceutically acceptable salts, esters and metal complexes thereof, wherein $R^1$ is hydrogen, $C_1-C_{10}$ alkylcarbonyl or unsubstituted or substituted $C_1-C_{10}$ alkyl where said substituent is amino or cyano;

$R^2$ and $R^3$ are hydrogen;

$R^2$ and $R^3$ together are oxo;

$R^4$ is hydrogen or $C_1-C_{10}$ alkylcarbonyl;

$R^5$ and $R^6$ are independently hydrogen, hydroxy or amino;

$R^5$ and $R^6$ together are oxo or oximino;

$R^7$ and $R^8$ are independently hydrogen, $C_1-C_{10}$ alkylcarbonyl, $C_1-C_{10}$ alkyl or phenylsulfonyl;

$R^9$ is hydrogen or $C_1-C_{10}$ alkylcarbonyl; and $R^{10}$ is hydrogen.

Salts and esters are generally prepared as acid addition salts by combining the core compound with one to three equivalents of an appropriate acid in an inert solvent. The salt is then recovered by solvent evaporation or by filtration if the salt precipitates spontaneously, or by precipitation using a co-solvent or a non-polar co-solvent followed by filtration.

Representative salts and esters include the following salts:

| | |
|---|---|
| Acetate | Iodide |
| Benzenesulfonate | Isothionate |
| Benzoate | Lactate |
| Bicarbonate | Lactobionate |
| Bisulfate | Laurate |
| Bitartrate | Malate |
| Borate | Maleate |
| Bromide | Mandelate |
| Calcium Edetate | Mesylate |
| Camsylate | Methylsulfate |
| Carbonate | Mucate |
| Chloride | Napsylate |
| Clavulanate | Nitrate |
| Citrate | Oleate |
| Dihydrochloride | Oxalate |
| Edetate | Pamoate (Embonate) |
| Edisylate | Palmitate |
| Estolate | Pantothenate |
| Esylate | Phosphate/diphosphate |
| Ethylsuccinate | Polygalacturonate |
| Fumarate | Salicylate |
| Gluceptate | Stearate |
| Gluconate | Subacetate |
| Glutamate | Succinate |
| Glycollylarsanilate | Tannate |
| Hexylresorcinate | Tartrate |
| Hydrabamine | Teoclate |
| Hydrobromide | Tosylate |
| Hydrochloride | Triethiodide |
| | Valerate |

DETAILED DESCRIPTION OF THE INVENTION

The term "pharmacologically effective amount" shall mean that amount of a drug or pharmaceutical agent that will elicit the biological or medical response of a tissue, system or animal that is being sought by a researcher or clinician.

The term "antibiotically effective amount" shall mean that amount of an antibiotic compound that will achieve a level of antibacterial activity at the site of infection that is sufficient to inhibit the bacteria in a manner that allows the host organism to overcome the infection.

The term "alkyl" shall mean cyclic or linear straight or branched chain alkane, alkene or alkyne of one to ten carbon atoms unless some designated number is given (e.g. $C_1-C_3$) with one or more degrees of unsaturation.

The term "aryl" shall include phenyl.

The term "substituted" shall be deemed to include multiple degrees of substitution by a named substituent.

Where multiple substituent moieties are disclosed or claimed, the substituted compound can be independently substituted by one or more of the disclosed or claimed substituent moieties, singly or plurally.

Whenever the terms "alkyl" or "aryl" or either of their prefix roots appear in a name of a substituent, (e.g., aralkoxyaryloxyalkyl) they shall be interpreted as including those limitations given above for "alkyl" and "aryl". Designated numbers of carbon atoms (e.g., C1-14) shall refer independently to the number of carbon atoms in an alkyl or cyclic alkyl moiety or to the alkyl portion of a larger substituent in which alkyl appears in the form of its prefix root.

The compounds of formula I can be prepared readily according to the following detailed descriptions and examples or modifications thereof using readily available starting materials, reagents and conventional synthesis procedures. The overall process is illustrated in the following flow sheet. In these reactions, it is also possible to make use of variants which are themselves known to those of ordinary skill in this art, but which are not mentioned in greater detail.

FLOW CHART

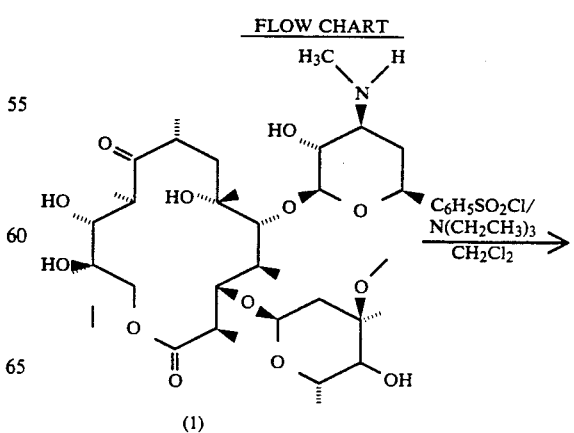

(1)

-continued
FLOW CHART
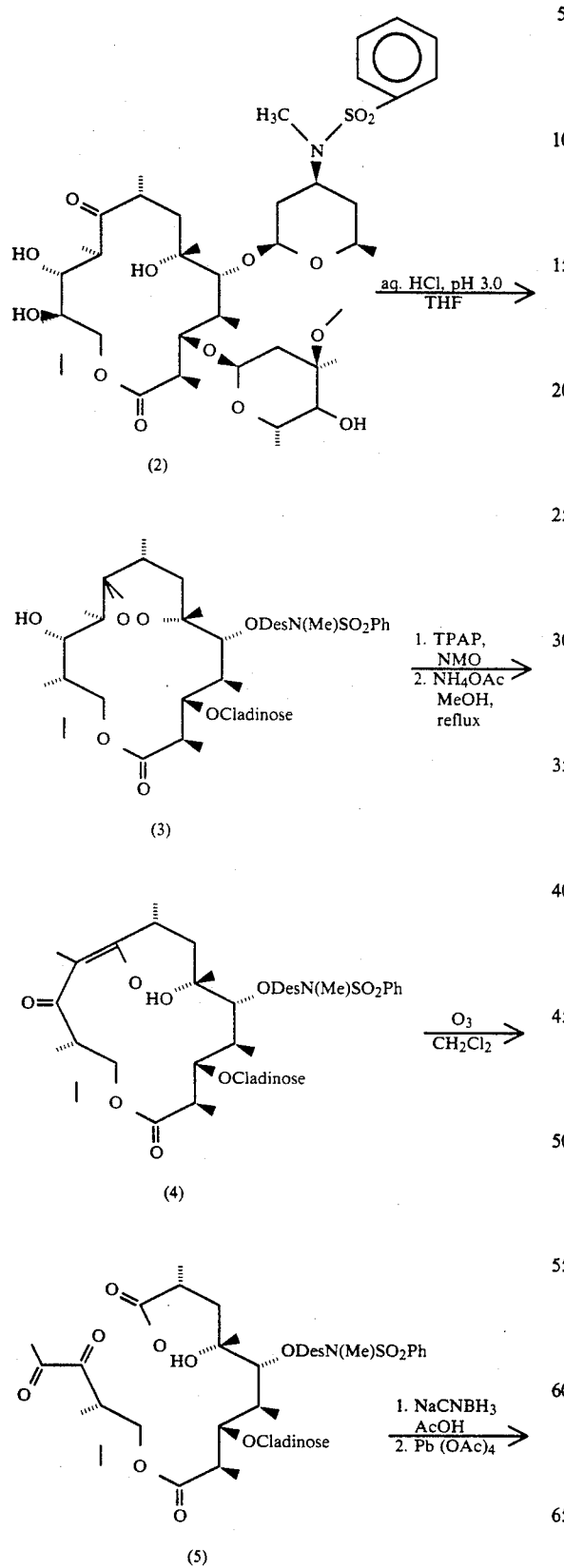
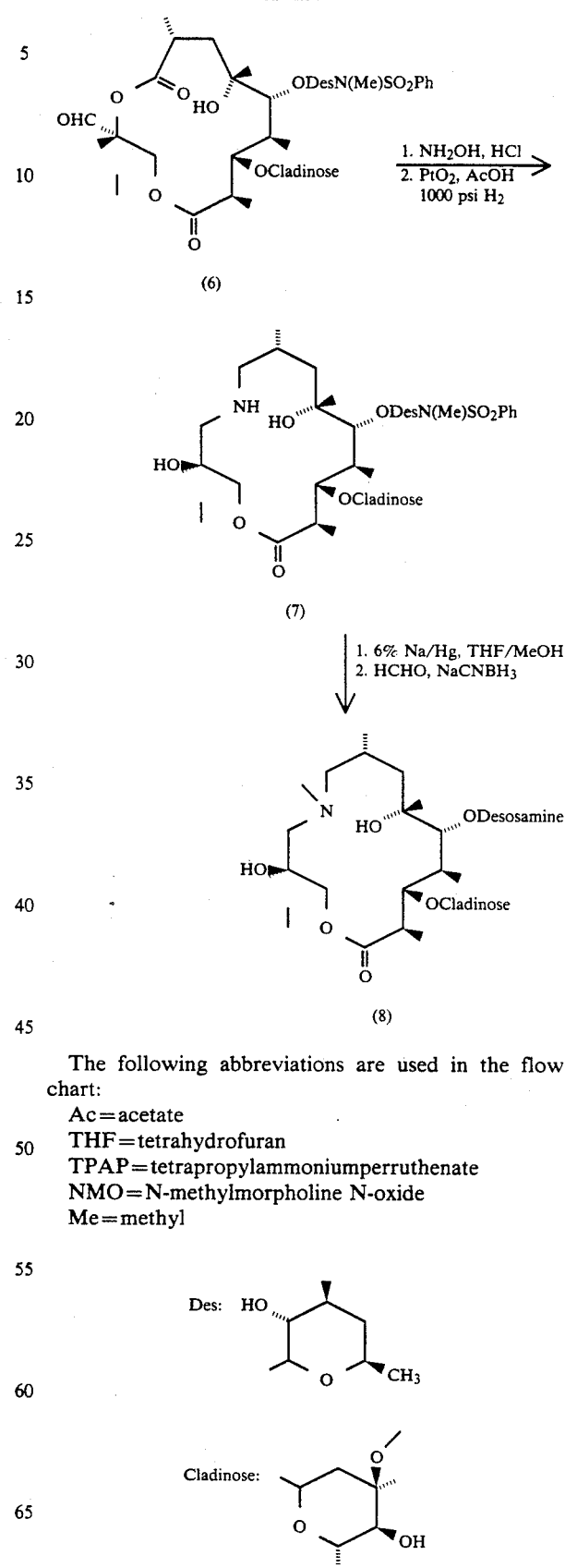
The following abbreviations are used in the flow chart:
Ac=acetate
THF=tetrahydrofuran
TPAP=tetrapropylammoniumperruthenate
NMO=N-methylmorpholine N-oxide
Me=methyl

EXAMPLE 1

3'-N-Desmethyl-3'-N-phenylsulfonyl erythromycin A

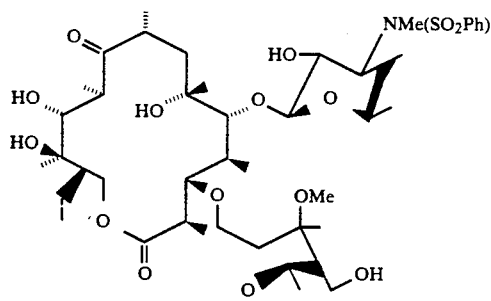

Erythromycin A (ErA) (50.0 g, 0.068 mol) was dissolved in 80/20 MeOH/H$_2$O (500 mL, 0.14N) and sodium acetate (28.0 g, 5.0 eq.) added. The mixture was warmed to 45°-50° C. and iodine (17.3 g, 1.0 eq.) added in one portion. The pH was monitored and maintained in the 8-9 range by addition of 2.5N sodium hydroxide solution, as required. After 2.5 h (tlc 90/10/1 CH$_2$Cl$_2$/MeOH/NH$_4$OH) the clear solution was poured into water containing ammonium hydroxide and extracted at pH 10-11 with methylene chloride. The extracts were dried over sodium sulphate, filtered and concentrated. The crude residue was dissolved in methylene chloride (500 mL) and triethylamine (28.5 mL, 3.0 eq.) added, followed by dropwise addition of benzene sulphonyl chloride (8.7 mL, 1.0 eq.). After 2 h (tlc 90/10/1 CH$_2$Cl$_2$/MeOH/NH$_4$OH) the mixture was diluted with saturated aqueous sodium bicarbonate solution and extracted with methylene chloride. The extracts were dried over sodium sulphate, filtered and concentrated. The residue was chromatographed (40-60% EtOAc/PhCH$_3$) to give the sulphonamide as a crunchy, white foam (47 g, 80%).

(This material proved to be fairly sensitive to acid, degrading to the 6,9-enol ether (as does ErA itself). Consequently nmr spectra were obtained in pyridine doped deuterochloroform. The compound exists in equilibrium with the two stereoisomers of the 6,9-hemiketal).

$^1$H (400 MHz, CDCl$_3$+1% d$_5$-py); data for keto form-δ7.84 (2H, d, J 7.6 Hz, o—SO$_2$Ph), 7.57-7.44 (3H, m, m/p—SO$_2$Ph), 5.03 (1H, dd, J 10.8, 2.0 Hz, H-13), 4.87 (1H, d, J 4.8 Hz, H-1''), 4.43 (1H, d, J 7.2 Hz, H-1'), 4.02-3.85 (4H, m, H-3, H-3', H-5'', OH), 3.78 (1H, s, H-11), 3.56-3.46 (2H, m, H-5, H-5'), 3.33 (3H, s, OMe), 3.27 (1H, m, H-2'), 3.09 (1H, s, OH), 3.08-2.98 (2H, m, H-10, H-4''), 2.84 (1H, m, H-2), 2.75 (3H, s, NMe), 2.66 (1H, m, H-8), 2.38-2.29 (3H, m, H-2'', 2'-OH, 4''-OH), 1.99-1.86 (2H, m, H-4, H-14), 1.82 (1H, dd, J 14.7, 11.4 Hz, H-7), 1.64-1.53 (2H, m, H-7, H-2'), 1.52-1.38 (5H, m, H-14, H-4', Me), 1.26-1.23 (6H, m, 5''-Me, Me), 1.19-1.09 (16H, m, H-4'', 2-Me, 8-Me, 10-Me, 5'-Me, Me), 1.03 (3H, d, J 7.6 Hz, 4-Me) and 0.82 (3H, t, J 7.3 Hz, 3H-15)ppm. $^{13}$C (CDCl$_3$+1% d$_5$-py); data for keto form-δ221.0, 175.6, 139.6, 132.4, 128.8, 127.2, 103.3, 96.2, 84.9, 79.9, 77.9, 76.9, 74.7, 74.5, 72.6, 70.6, 68.7, 67.9, 65.5, 57.9, 49.4, 44.8, 44.7, 39.0, 38.4, 38.2, 35.9, 34.9, 28.3, 26.5, 21.5, 21.1, 20.8, 18.4, 18.3, 16.2, 15.9, 12.0, 10.6 and 9.5 ppm.

Data for hemi-ketal tautomers - δ179.2, 176.1, 139.7, 131.8, 128.3, 127.8, 110.3, 107.2, 106.4, 103.1, 99.0, 95.4, 87.3, 84.1, 83.8, 83.4, 82.1, 81.9, 80.7, 77.9, 77.6, 75.4, 72.8, 72.4, 72.3, 70.3, 69.7, 68.6, 68.0, 66.2, 65.6, 58.0, 57.6, 53.4, 49.6, 48.6, 45.0, 43.1, 41.6, 41.6, 41.4, 37.4, 37.3, 36.4, 34.7, 29.6, 28.8, 28.2, 27.1, 24.9, 24.1, 21.8, 21.5, 21.4, 20.7, 20.6, 18.0, 17.7, 17.5, 17.1, 17.0, 16.8, 14.0, 13.8, 11.2, 11.1, 10.4 and 9.2 ppm.

IR (CHCl$_3$) 3600, 3520, 2975, 1730, 1690, 1510, 1375, 1340, 1160 and 1050 cm$^{-1}$.

FABMS (Li spike) m/z 866 (M$^+$+Li)

Analysis calcd. for C$_{42}$H$_{69}$O$_{15}$NS: C, 58.65; H, 8.09; N, 1.63%. Found: C, 58.70; H, 7.98; N, 1.49%.

EXAMPLE 2

3'-N-Desmethyl-3'-N-phenylsulfonylanhydro erythromycin A

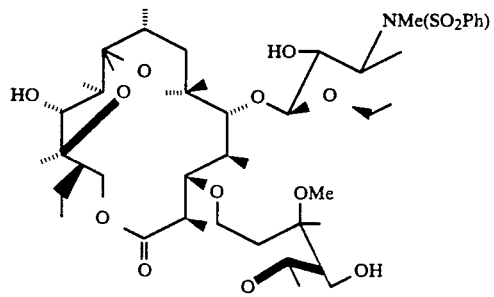

The product of Example 1 (47.0 g, 0.055 mol) was dissolved in 5:1 THF/H20 (1000 mL, 0.05N) at room temperature and the pH adjusted to 3.0 by addition of 2N hydrochloric acid. After ~9 h (tlc 60% EtOAc/PhCH$_3$) the mixture was poured into water containing ammonium hydroxide and extracted at pH 10-11 with methylene chloride, dried over sodium sulphate, filtered and concentrated. The residue was chromatographed (20-50% EtOAc/PhCH$_3$) to give the spiroketal as a white foam (30 g, 65%).

$^1$H (400 MHz, CDCl$_3$); δ7.85 (2H, d, J 7.3 Hz, o—SO$_2$Ph), 7.58-7.46 (3H, m, m/p—SO$_2$Ph), 5.14 (2H, m, H-13, H-1''), 4.29 (1H, dd, J 7.0, 3.4 Hz, H-3), 4.25 (1H, d, J 7.2 Hz, H-1'), 3.97 (2H, m, H-3', H-5''), 3.48 (2H, m, H-11, H-5'), 3.41 (1H, d, J 5.2 Hz, H-5), 3.27 (4H, m, H-2', OMe), 3.12 (1H, m, H-2), 2.98 (2H, m, H-10, H-4''), 2.75 (3H, s, NMe), 2.38 (1H, d, J 2.6 Hz, 2'-OH), 2.35-2.21 (3H, m, H-8, H-2'', 4''-OH), 2.10-1.88 (3H, m, H-4, H-14, 11-OH), 1.64 (1H, m, H-14), 1.50 (1H, dd, J 15.4, 4.8 Hz, H-2''), 1.45 (1H, dd, J 11.4, 5.5 Hz, H-7), 1.41-1.36 (4H, m, H-4', Me), 1.28-1.15 (13H, m, H-4', 10-Me (1.22, d, J 7.3 Hz), 5''-Me (1.18, d, J 6.9 Hz), Me (1.26, s), Me (1.19, s)), 1.12 (3H, d, J 6.1 Hz, 5'-Me), 1.10-1.00 (10H, m, H-7, 2-Me (1.05, d, J 7.7 Hz), 4-Me (1.08, d, J 7.4 Hz), 8-Me (1.02, d, J 6.7 Hz)) and 0.81 (3H, t, J 7.3 Hz, 3H-15) ppm.

$^{13}$C (CDCl$_3$); 178.6, 139.5, 132.6, 129.0, 127.3, 115.8, 102.9, 95.2, 87.1, 86.6, 82.3, 81.6, 81.5, 78.2, 76.2, 72.7, 69.5, 68.5, 65.1, 58.2, 51.7, 49.3, 46.3, 43.5, 41.4, 41.3, 35.7, 34.5, 28.6, 28.4, 25.0, 24.4, 21.6, 20.8, 17.8, 16.2, 13.9, 12.2 and 10.9 ppm.

IR (film) 3440, 2970, 2935, 2880, 1730, 1450, 1375, 1330, 1155, 1040, 1000, 900 and 750 cm$^{-1}$. FABMS (Li spike) m/z 848 (M$^+$+Li)

Analysis cald. for C$_{42}$H$_{67}$O$_{14}$NS.H$_2$O: C, 58.67; H, 7.80; N, 1.63%. Found: C, 58.70; H, 7.98; N, 1.49%.

EXAMPLE 3

3'-N-Desmethyl-3'-N-phenylsulfonyl-11-oxo anhydro erythromycin A

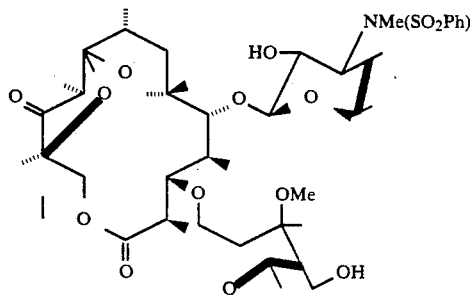

The product of Example 2 (27.0 g, 0.032 mol) was dissolved in methylene chloride (320 mL, 0.1N) at room temperature. N-Methylmorpholine N-oxide (4.5 g, 1.2 eq.) was added, followed by tetrapropylammonium perruthenate (1.0 g, 0.09 eq.). After 30 min (tlc 40% EtOAc/PhCH$_3$) the mixture was filtered through silica gel (50% CH$_2$Cl$_2$/Et$_2$O) to remove the catalyst. The filtrate was concentrated and chromatographed (20–30% EtOAc/PhCH$_3$) to give the ketone as a white foam (16 g, 59%).

$^1$H (400 MHz, CDCl$_3$); δ7.82 (2H, d, J 7.3 Hz, o—SO$_2$Ph), 7.60–7.45 (3H, m, m/p—SO$_2$Ph), 5.23 (1H, d, J 4.8 Hz, H-1″), 5.07 (1H, dd, J 11.3, 3.3 Hz, H-13), 4.45 (1H, dd, J 9.8, 1.8 Hz, H-3), 4.29 (1H, d, J 7.2 Hz, H-1'), 3.95 (2H, m, H-3', H-5″), 3.54–3.45 (2H, overlapping m and d(J 2.4 Hz), H-5, H-5'), 3.34 (1H, q, J 7.5 Hz, H-10), 3.25 (3H, s, OMe), 3.24–3.11 (2H, m, H-2, H-2'), 2.96 (1H, apparent t, J 10.3 Hz, H-4″), 2.74 (3H, s, NMe), 2.45–2.35 (2H, m, H-8, H-7), 2.26 (1H, d, J 10.3 Hz, 4″-OH), 2.22 (1H, d, J 15.1 Hz, H-2″), 2.18 (1H, d, J 2.4 Hz, 2'-OH), 2.09 (1H, m, H-4), 1.60–1.43 (4H, m, H-7, 2H-14, H-2″), 1.42 (3H, s, Me), 1.37–1.26 (2H, m, 2H-4'), 1.24–1.19 (6H, overlapping s and d, Me, 10-Me), 1.18–1.10 (12H, overlapping s and 3 xd, Me, 4-Me, 5'-Me, 5″Me), 0.97 (6H, d, J 7.3 Hz, 2-Me, 8-Me) and 0.76 (3H, t, J 7.0 Hz, 3H-15) ppm.

$^{13}$C (CDCl$_3$); 216.2, 178.4, 139.3, 132.8, 129.1, 127.2, 114.9, 102.2, 94.2, 86.7, 85.4, 81.0, 79.2, 78.2, 74.9, 72.8, 69.3, 68.6, 65.1, 58.5, 51.7, 49.4, 45.6, 42.3, 41.7, 41.4, 35.6, 34.5, 28.7, 26.7, 22.7, 21.6, 20.9, 19.8, 19.0, 17.9, 12.8, 12.2, 10.8 and 9.8 ppm.

IR (film); 3520, 2970, 2935, 2880, 1740, 1460, 1450, 1375, 1330, 1160, 1050, 1000 and 750 cm$^{-1}$.

FABMS (Li spike) m/z 846 (M$^+$+Li)

Analysis, calcd for C$_{42}$H$_{65}$O$_{14}$NS: C, 60.05: H, 7.80: N, 1.67%. Found: C, 59.55: H, 7.92: N, 1.65%.

EXAMPLE 4

9,10-Dehydro-3'-N-desmethyl-9-deoxo-12-deoxy-9,12-epoxy-11-oxo-3'N-phenylsulfonyl erythromycin A

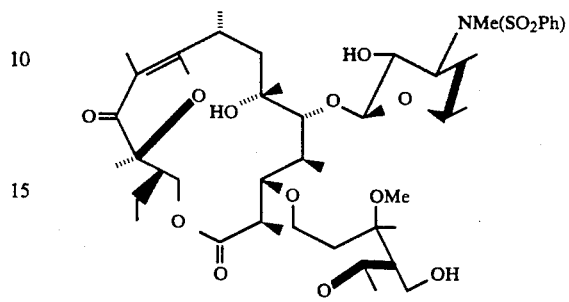

The product of Example 3 (16.0 g, 0.019 mol) was dissolved in methanol (190 mL, 0.1N) and ammonium acetate (8.8 g, 6.0 eq.) added. The mixture was heated to reflux. After 90 min (tlc 40% EtOAc/PhCH$_3$) the mixture was allowed to cool to room temperature and poured into dilute aq.sodium bicarbonate solution, extracted with methylene chloride, dried over sodium sulphate, filtered and concentrated. The residue was filtered through silica gel (50% Et$_2$O/CH$_2$Cl$_2$) to give the furanone as a white foam (14.5 g, 90%).

$^1$H (400 MHz, CDCl$_3$); δ 7.87 (2H, d, J 7.3 Hz, o—SO$_2$Ph), 7.52–7.41 (3H, m, m/p—SO$_2$Ph), 5.00 (1H, dd, J 10.8, 3.1 Hz, H-13), 4.83 (1H, br s, 6-OH), 4.71 (1H, dd, J 4.5, 2.0 OHz, H-1″), 4.51 (1H, d, J 7.3 Hz, H-1'), 4.05 (2H, m, H-3', H-5″), 3.98 (1H, d, J 3.2 Hz, 2'-OH), 3.94 (1H, dd, J 6.4, 2.9 Hz, H-3), 3.71 (2H, m, H-5, H-5'), 3.32 (1H, ddd, J 10.3, 7.3, 3.4 Hz, H-2'), 3.25 (3H, s, OMe), 3.00 (1H, apparent t, J 9.0 H-4″), 2.90 (1H, m, H-8), 2.74 (3H, s, NMe), 49 (1H, d, J 9.4 Hz, 4″-OH), 2.43 (1H, m, H-2), 2.31 (1H, dd, J 15.0, 2.2 Hz, H-2″), 2.14 (1H, m, H-7), 2.02 (1H, m, H-14), 1.82–1.73 (2H, m, H-7, H-14), 1.70 (3H, s, 10-Me), 1.63–1.48 (4H, m, H-4, 2H-4', H-2″), 1.34 (3H, s, Me), 1.32 (3H, d, J 7.1 Hz, 8-Me), 1.23 (3H, s, Me), 1.28–1.21 (9H, m, Me, 5'-Me, 5″-Me), 1.16 (3H, d, J 7.0 OHz, 2-Me), 0.95 (3H, d, J 7.3 Hz, 4-Me) and 0.88 (3H, t, J 7.4 Hz, 3H-15) ppm.

$^{13}$C (CDCl$_3$); 204.9, 192.7, 175.6, 139.9, 132.1, 128.5, 127.5, 108.4, 105.2, 96.6, 88.3, 87.3, 79.1, 77.8, 76.9, 74.5, 72.9, 69.8, 69.0, 66.8, 65.8, 57.6, 49.1, 46.6, 43.0, 41.7, 36.2, 35.2, 31.4, 28.3, 26.3, 21.7, 21.5, 21.2, 20.5, 17.4, 15.2, 14.5, 10.6 and 5.9 ppm.

IR (Film); 3450, 2970, 2930, 2880, 1735, 1690, 1615, 1450, 1375, 1330, 1160 and 750 cm$^{-1}$.

FABMS (Li spike) m/z 846 (M$^+$+Li)

Analysis, calcd for C$_{42}$H$_{65}$O$_{14}$NS: C, 60.05: H, 7.80: N, 1.67%. Found: C, 59.97: H, 7.85: N, 1.65%.

EXAMPLE 5

8,12-O-Carbonyloxo-3'-N-desmethyl-12-(1,2-dioxo-propyl)-9,10,11-nor-3'-N-phenylsulfonyl erythromycin A

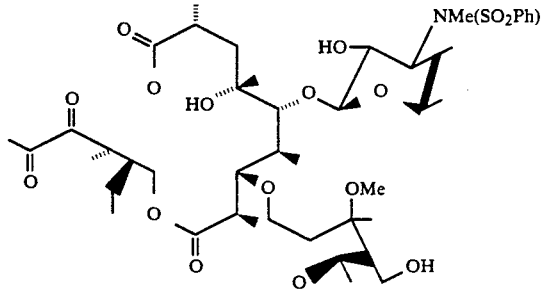

The product of Example 4 (14.5 g, 0.017 mol) was dissolved in 1:1 methylene chloride/pyridine (175 mL, 0.1N) and cooled to $-78°$ C. A stream of ozone in oxygen was passed through the mixture. After 2 h (tlc 40% EtOAc/PhCH$_3$) the ozone was turned off and oxygen passed through the solution for a further 5 min. Dimethyl sulphide (6.3 mL, 5.0 eq.) was added dropwise and the mixture allowed to warm to room temperature. After 5 min at room temperature the mixture was concentrated and then reconcentrated three times from methylene chloride/heptane (to remove pyridine). The residue was filtered through silica gel (50% CH$_2$Cl$_2$/Et$_2$O) to give the diketone as a pale yellow foam (12.9 g, 86%).

$^1$H (400 MHz, CDCl$_3$); δ7.85 (2H, d, J 7.3 Hz, o—SO$_2$Ph), 7.55–7.40 (3H, m, m/p—SO$_2$Ph), 5.08 (1H, dd, J 7.9, 5.7 Hz, H-13), 4.74 (1H, d, J 4.3 Hz, H-1″), 4.50 (1H, d, J 7.2 Hz, H-1′), 4.24 (1H, dd, J 5.7, 1.9 Hz, H-3), 4.03–3.97 (3H, m, OH, H-3′, H-5″), 3.69 (1H, d, J 5.4 Hz, H-5), 3.62 (1H, m, H-5′), 3.37 (1H, br, OH), 3.34–3.24 (4H, m, OMe, H-2′), 2.97 (1H, apparent t, J 9.5 Hz, H-4″), 2.76–2.62 (5H, m, NMe, H-2, H-8), 2.39–2.32 (2H, m, H-2″, 4″-OH), 2.29 (3H, s, MeCOCO-), 2.14–2.02 (2H, m, H-4, H-7), 1.66–1.42 (8H, m, Me, 2H-14, 2H-4′, H-2″), 1.34 (1H, dd, J 15.1, 6.0 Hz, H-7), 1.23 (3H, s, Me), 1.21 (3H, d, J 7.0 Hz, 8-Me), 1.20–1.14 (12H, m, Me, 2-Me, 5′-Me, 5″-Me), 1.01 (3H, d, J 7.0 Hz, 4-Me) and 0.85 (3H, t, J 7.2 Hz, 3H-15) ppm.

$^{13}$C (CDCl$_3$); 196.2, 193.9, 177.1, 176.1, 139.7, 132.2, 128.6, 127.4, 104.2, 96.8, 86.4, 84.6, 79.1, 77.4, 74.7, 72.7, 70.0, 68.6, 66.1, 57.6, 49.3, 45.5, 42.4, 39.4, 36.0, 34.9, 34.5, 28.3, 26.2, 24.8, 23.3, 21.5, 20.6, 18.8, 17.7, 14.1, 10.7 and 10.0 ppm.

IR (Film) 3480(br.), 2980, 2940, 1725, 1455, 1375, 1330, 1160, 1050 and 730 cm$^{-1}$.

FABMS (Li spike) m/z 877

Analysis calcd for C$_{42}$H$_{65}$O$_{16}$NS: C, 57.85; H, 7.51; N, 1.61%. Found: C, 57.63; H, 7.56; N, 1.52%.

EXAMPLE 6

8,12-O-Carbonyloxo-3'-N-desmethyl-12-formyl-9,10,11-nor-3'-N-phenylsulfonyl erythromycin A

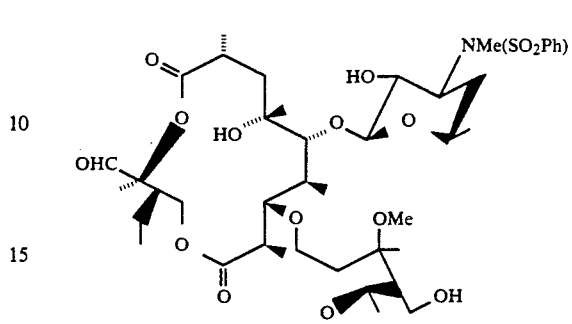

The product of Example 5 (10.5 g, 0.012 mol) was dissolved in acetic acid (120 mL, 0.1N) at room temperature. Sodium cyanaborohydride (2.3 g, 3.0 eq.) was added in portions over ~5 min. After 30 min (tlc 40% EtOAc/PhCH$_3$) the mixture was diluted with water and extracted once with methylene chloride. The aqueous portion was adjusted to pH 10 with 5N sodium hydroxide solution and extracted with methylene chloride. The acidic extract was washed with dilute aq. sodium hydroxide and combined with the alkaline extracts. The combined organics were washed with brine, dried over magnesium sulphate, filtered and concentrated. The residue was dissolved in methylene chloride (120 mL) and lead tetraacetate (5.3 g, 1.0 eq.) added in one portion. After 30 min (tlc 40% EtOAc/PhCH$_3$) the mixture was poured into dilute aq. sodium bicarbonate solution and extracted with methylene chloride. The organics were washed three times with water, then once with brine and dried over magnesium sulphate, filtered and concentrated. The residue was chromatographed (20–30% EtOAc/PhCH$_3$) to give the aldehyde as a white foam (5.1 g, 51%).

$^1$H (400 MHz, CDCl$_3$); δ9.48 (1H, s, CHO), 7.85 (2H, d, J 7.3 Hz, o—SO$_2$Ph), 7.58–7.40 (3H, m, m/p—SO$_2$Ph), 5.13 (1H, dd, J 10.3, 2.6 Hz, H-13), 4.87 (1H, d, J 4.4 Hz, H-1″), 4.55 (1H, d, J 7.3 Hz, H-1′), 4.28 (1H, br s, H-3), 4.07–3.92 (2H, m, H-3′, H-5″), 3.67 (1H, d, J 5.9 Hz, H-5), 3.62 (1H, m, H-5′), 3.52 (1H, br s, 6-OH), 3.35–3.24 (4H, m, OMe, H-2′), 3.03 (1H, apparent t, J 9.5 Hz, H-4″), 2.81 (1H, m, H-8), 2.75 (3H, s, NMe), 2.72 (1H, d, J 2.5 Hz, 2′-OH), 2.66 (1H, m, H-2), 2.41 (1H, d, J 9.9 Hz, 4″-OH), 2.39 (1H, d, J 15.8 Hz, H-2″), 2.04–1.94 (2H, m, H-4, H-7), 1.72–1.35 (9H, m, Me, H-7, 2H-14, 2H-4′, H-2″), 1.28 (3H, d, J 6.7 Hz, 8-Me), 1.26 (3H, s, Me), 1.24 (3H, d, J 6.5 Hz, 5″-Me), 1.19 (6H, m, Me, 2-Me), 1.15 (3H, d, J 6.1 Hz, 5′-Me), 1.04 (3H, d, J 7.0 Hz, 4-Me) and 0.85 (3H, t, J 7.3 Hz, 3H-15) ppm.

$^{13}$C (CDCl$_3$); 197.7, 176.6, 176.1, 139.6, 132.4, 128.8, 127.3, 103.3, 96.3, 85.1, 84.4, 78.0, 77.5, 75.1, 72.8, 70.4, 68.6, 66.0, 57.6, 49.3, 44.5, 42.5, 41.1, 41.0, 35.9, 35.6, 34.9, 28.3, 22.6, 21.6, 20.7, 17.9, 17.7, 13.6, 10.4 and 10.0 ppm.

IR (Film); 3500(br.), 2975, 2940, 1735, 1455, 1380, 1335, 1160, 1050, 995, 785 and 730 cm$^{-1}$.

FABMS (Li spike) m/z 836 (also 868 (M$^+$+K) and 990 (M$^+$+dithioerythritol)).

Analysis calcd for C$_{40}$H$_{63}$O$_{15}$NS: C, 57.89; H, 7.65; N, 1.69%. Found: C, 57.92; H, 7.78; N, 1.64%.

EXAMPLE 7

8,12-O-Carbonyloxo-3′-N-desmethyl-9,10,11-nor-12-oximinoformyl-3′-N-phenylsulfonyl erythromycin A.

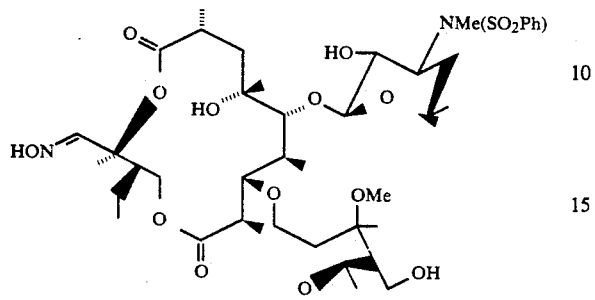

The product of Example 6 (6.1 g, 7.4 mmol) was dissolved in pyridine (70 mL, 0.1N) and hydroxylamine hydrochloride (2.6 g, 5.0 eq.) added. The mixture was heated to 60° C. After 90 min (tlc 40% EtOAc/PhCH$_3$) it was allowed to cool to room temperature and poured into dilute aq. sodium bicarbonate solution. The mixture was extracted with methylene chloride, dried over magnesium sulphate, filtered and concentrated. The residue was reconcentrated three times from methylene chloride/heptane (to remove pyridine) and filtered through silica gel (50% CH$_2$Cl$_2$/Et$_2$O) to give the oxime as a white foam (5.8 g, 93%).

$^1$H (400 MHz, CDCl$_3$, mixture of oxime geometric isomers); δ8.05-7.90 (1H, br, —NOH), 7.83 (2H, d, J 7.3 Hz, o—SO$_2$Ph), 7.56-7.41 (4H, m, m/p—SO$_2$Ph, HON-CH—), 5.17 (1H, dd, J 10.0, 2.6 Hz, H-13), 4.87 (1H, d, J 4.7 Hz, H-1″), 4.52 (1H, d, J 7.1 Hz, H-1′), 4.17 (1H, br d, J 4.9 Hz, H-3), 4.04-3.92 (2H, m, H-3′, H-5″), 3.65-3.55 (2H, m, H-5′), 3.38-3.24 (5H, m, OMe (as two s, one for each isomer, 0.003 ppm apart), H-2′, 6-OH), 3.03 (1H, apparent t, J 9.6 Hz, H-4″), 2.74 (3H, 2xs, NMe (s from each isomer, 0.004 ppm apart)), 2.72-2.62 (3H, m, H-2, H-8, 2′-OH), 2.44 (1H, d, J 10.0 Hz, 4″-OH), 2.39 (1H, d, J 15.1 Hz, H-2″), 2.00 (1H, m, H-4), 1.93 (1H, dd, J 14.9, 5.1 Hz, H-7), 1.66-1.36 (9H, m, Me, H-7, 2H-14, 2H-4′, H-2″), 1.28-1.10 (18H, m, Me, Me, 2-Me, 8-Me, 5′Me, 5″-Me), 1.03 (3H, d, J 7.0 Hz, 4-Me) and 0.86 (3H, two overlapping t, (one from each isomer), J 7.3 Hz, 3H-15) ppm.

$^{13}$C (CDCl$_3$); 176.1, 175.8, 150.4, 139.7, 132.4, 128.8, 127.4, 103.3, 96.3, 84.4, 81.6, 78.7, 77.7, 75.1, 72.8, 70.5, 68.5, 65.9, 57.6, 49.4, 44.6, 42.0, 40.5, 36.6, 36.0, 34.9, 28.4, 25.6, 23.1, 21.6, 20.7, 19.5, 18.0, 17.9, 13.8, 10.4 and 9.9 ppm.

IR (Film); 3450(br.), 2975, 2940, 1735, 1455, 1380, 1330, 1160, 1050 and 950 cm$^{-1}$.

FABMS (Li spike) m/z 851

Analysis calcd for C$_{40}$H$_{64}$O$_{15}$NS: C, 56.86; H, 7.63; N, 3.32%. Found: C, 56.45; H, 7.70; N, 3.15%.

EXAMPLE 8

10-Aza-11-deoxy-10,3′-N-didesmethyl-3′-N-phenylsulfonyl erythromycin A$^{(1)}$;
10-Aza-9,10-dehydro-9-deoxo-10,3′-N-didesmethyl-11,12-dideoxy-9,12-epoxy-3′-N-phenyl-sulfonyl erythromycin A$^{(2)}$; and
10-Aza-11-deoxy-9-deoxo-10,3′-N-didesmethyl-3′-N-phenylsulfonyl erythromycin A$^{(3)}$.

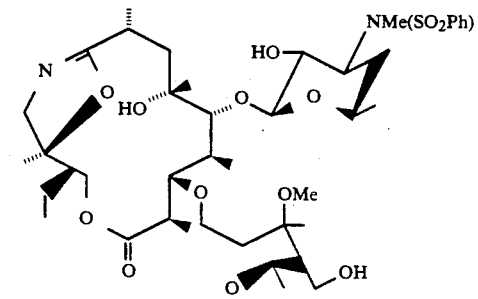

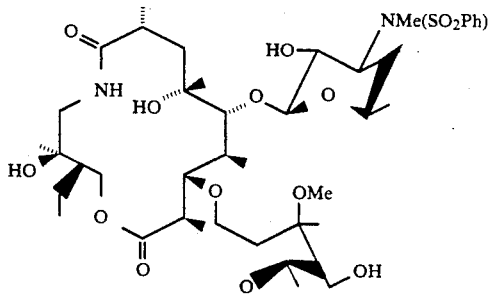

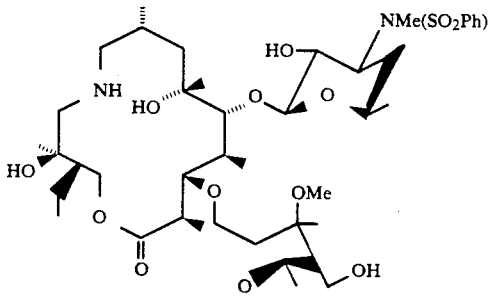

The product of Example 7 (3.75 g, 4.4 mmol) was dissolved in acetic acid (40 mL, 0.1N) and platinum oxide (1.8 g, 0.5 wt eq) added. The mixture was hydrogenated at room temperature under 1000 psi hydrogen pressure for 48 h. The mixture was filtered through a pad of celite ®, eluting with dichloromethane, and concentrated. The residue was re-concentrated three times from dichloromethane/heptane (to remove acetic acid). The resulting white foam was carefully chromatographed (80% EtOAc/PhCH$_3$; EtOAc; 95/5 CH$_2$Cl$_2$/MeOH; 95/5/1–90/10/1 CH$_2$Cl$_2$/MeOH/N-H$_4$OH) to give recovered aldoxime (1.56 g, 42%), lactam (100 mg, 5%), impure imino-ether and amine (700 mg, 33%). Further careful chromatography (EtOAc) or plc (triple elution, EtOAc) gave clean imino-ether (90 mg, 4%).

Note: all components were contaminated with traces (~5%) of inseperable cyclohexyl sulphonamide analogues (from reduction of the benzene sulphonamide).

This precluded adequate microanalysis. Selected data is given.

(1)

$^1$H (400 MHz; CDCl$_3$); δ7.82 (2H, d, J 7.3 Hz, o—SO$_2$Ph), 7.77–7.44 (3H, m, m/p—SO$_2$Ph), 6.79 (1H, br d, J 9.5 Hz, NH), 4.78 (1H, br d, J 11.1 Hz, H-13), 4.71 (1H, d, J 4.4 Hz, H-1″), 4.64 (1H, d, J 7.3 Hz, H-1′), 4.27 (1H, d, J 2.6 Hz, H-3), 4.15 (1H, ddd, J 13.8, 10.3, 1.6 Hz, H-11), 4.05 (2H, m, H-3′, H-5″), 3.85 (1H, d, J 5.1 Hz, H-5), 3.75 (1H, s, 6-OH), 3.61 (1H, m, H-5′), 3.41 (3H, s, OMe), 3.37 (1H, ddd, J 10.6, 7.6, 2.1 Hz, H-2′), 3.09 (1H, apparent t, J 9.7 Hz, H-4″), 2.74 (3H, s, NMe), 2.64 (1H, d, J 14.5 Hz, H-11), 2.50 (2H, m, H-2, H-8), 2.38 (1H, d, J 15.4 Hz, H-2″eq), 2.30 (1H, br s, 2′-OH), 2.27 (1H, d, J 9.9 Hz, 4″-OH), 2.13 (1H, d, J 1.9 Hz, 12-OH), 1.98 (1H, m, H-14), 1.81 (3H, m, H-4, H-7, H-4′), 1.60 (1H, d, J 15.6 Hz, H-7), 1.55 (1H, dd, J 15.5, 4.7 Hz, H-2″ax), 1.45 (2H, m, H-14, H-4′), 1.39 (3H, d, J 6.6 Hz, 2-Me), 1.31 (3H, d, J 6.2 Hz, 5″-Me), 1.26 (3H, s, Me), 1.20 (6H, m, Me, 8-Me), 1.14 (3H, d, J 6.2 Hz, 5′-Me), 1.05 (6H, m, Me, 4-Me) and 0.82 (3H, t, J 7.2 Hz, 3H-15) ppm.

$^{13}$C (CDCl$_3$); 177.9, 176.7, 139.4, 132.6, 128.9, 127.3, 101.8, 95.0, 82.8, 81.2, 77.5, 76.2, 75.6, 74.6, 72.6, 70.3, 68.5, 66.6, 57.4, 49.4, 43.8, 43.3, 42.1, 39.6, 36.5, 35.7, 34.7, 28.3, 26.5, 23.3, 22.7, 21.7, 20.6, 20.2, 17.6, 11.5, 11.3, 10.9 ppm.

IR (Film); 3500, 3360, 2980, 2940, 1725, 1655, 1535, 1455, 1380, 1325, 1205, 1160, 1050, 995, 945, 785, 730 and 690 cm$^{-1}$.

FABMS (Li spike); m/z 837

(2)

$^1$H (400 MHz; CDCl$_3$): δ7.88 (2H, d, J 7.3 Hz, o—SO$_2$Ph), 7.58–7.41 (3H, m, m/p—SO$_2$Ph), 4.88–4.80 (2H, m, H-13, H-1″), 4.65 (1H, d, J 7.4 Hz, H-1′), 4.44 (1H, br s, 6-OH), 4.15–4.05 (2H, m, H-3′, H-5″), 3.99 (1H, br s, H-3), 3.94 (1H, d, J 13.8 Hz, H-11), 3.76 (1H, d, J 3.4 Hz, H-5), 3.65 (1H, m, H-5′), 3.38–3.31 (2H, m, H-11, H-2′), 3.28 (3H, s, OMe), 3.11 (1H, apparent t, J 7.7 Hz, H-4″), 2.79–2.72 (4H, m, NMe, 4″-OH), 2.62 (1H, m, H-8), 2.53 (1H, m, H-2), 2.34 (1H, dd, J 14.7 Hz, 3.5 Hz, H-2″eq), 2.18 (1H, br d, J 14.6 Hz, H-7), 1.80–1.40 (7H, m, H-4, H-7, 2H-14, 2H-4′, H-2″ax), 1.35 (3H, s, Me), 1.33 (3H, d, J 7.0 Hz, 8-Me), 1.28–1.24 (6H, m, Me, 5″-Me), 1.17 (6H, d, J 6.3 Hz, coincident 2Me, 5′-Me), 1.13 (3H, s, Me), 0.98 (3H, d, J 7.0 Hz, 4-Me) and 0.94 (3H, t, J 7.4 Hz, 3H-15)ppm.

$^{13}$C (CDCl$_3$); 176.4, 172.9, 139.9, 132.2, 128.7, 127.5, 104.9, 96.1, 87.6 (br), 86.3, 79.6, 79.3, 76.5, 75.4, 73.3, 70.2, 68.8, 67.8, 60.4, 57.5, 49.0, 44.8, 42.7, 42.2, 36.1, 35.3, 28.3, 28.2, 24.0, 23.3, 21.5, 20.6, 17.4, 13.2, 10.6, 10.0 ppm.

IR (Film); 3450, 2970, 2035, 1730, 1665, 1450, 1380, 1330, 1160, 1050, 990, 750 cm$^{-1}$.

FABMS (li spike) m/z 820

(3)

$^1$H (400 MHz, CDCl$_3$); B 7.83 (2H, d, J 7.3 Hz, o—SO$_2$Ph), 7.57–7.42 (3H, m, m/p—SO$_2$Ph), 4.94 (1H, d, J 11.0 Hz, H-13), 4.79 (1H, d, J 7.2 Hz, H-1′), 4.64 (1H, br s, H-3), 4.54 (1H, d, J 4.7 Hz, H-1″), 4.03 (1H, m, H-3′), 3.90 (2H, m, H-5, H-5″), 3.67 (1H, m, H-5′), 3.40–3.32 (4H, m, OMe, H-2′), 3.07 (1H, apparent t, J 9.2 Hz, H-4″), 3.01 (1H, d, J 12.5 Hz, H-11), 2.74 (3H, s, NMe), 2.51 (1H, q, J 7.0 0Hz, H-2), 2.44 (1H, apparent t, J 10.6 Hz, H-9), 2.38–2.25 (4H, m, H-9, H-11, H-2″eq, 4″-OH), 1.95 (1H, br s, H-8), 1.83 (1H, br s, H-4), 1.67–1.31 (6H, m, H-7, 2H-14, 2H-4′, H-2″ax), 1.28–1.16 (10H, m, H-7, Me, 2-Me, 5″-Me), 1.14 (6H, m, Me, 5′-Me), 1.09 (6H, m, Me, 8-Me), 1.04 (3H, d, J 7.3 Hz, 4-Me) and 0.86 (3H, t, J 7.1 Hz, 3H-15)ppm.

$^{13}$C (CDCl$_3$); 175.7, 139.5, 132.5, 128.8, 127.3, 100.9, 94.4, 82.3, 80.6, 77.6, 76.1, 74.6, 72.9, 71.2, 70.6, 68.3, 66.1, 61.8, 58.5, 57.1, 56.0, 49.2, 43.4, 42.5, 41.5, 35.8, 34.3, 30.8, 28.2, 24.6, 24.2, 24.0, 21.9, 21.2, 20.5, 17.8, 11.4, 11.0, 10.5 ppm.

IR (Film); 3480, 2930, 1730, 1460, 1380, 1320, 1185, 1155, 1125, 1050, 995, 945, 750 cm$^{-1}$.

FABMS (Li spike) m/z 823 (M$^+$+Li), 817 (M$^+$+1)

EXAMPLE 9

10-Aza-10-desmethyl-11-deoxy erythromycin A

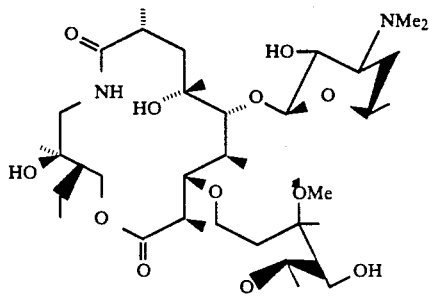

Napthalene (0.5 g, 3.9 mmol) was dissolved in THF (3.9 mL, 1.0N) at room temperature and freshly cut lithium pieces (55 mg, 2 eq) added. The mixture was sonicated for 45 min. Portions of this solution of lithium napthalenide were added dropwise to a solution of the sulphonamide (80 mg, 96 μmol) in THF (1.0 mL, 0.1N) maintained at −78° C., until the deep green colour of the reagent was no longer quenched. The mixture was allowed to stir for a further 10 min before quenching with aq.sodium bicarbonate solution and allowing to warm to room temperature. Potassium carbonate solution was added and the mixture extracted with methylene chloride. The organics were dried over magnesium sulphate, filtered and concentrated. The residue was crudely chromatographed (95:5 CH$_2$Cl$_2$/MeOH; 90:10:1 CH$_2$Cl$_2$/MeOH/NH$_4$OH) to remove napthalene. The resulting clear oil was dissolved in chloroform (2 mL, 0.05N). Formaldehyde (31 μL of 37% aq solution, 4 eq) was added followed by formic acid (7.3 μL, 2 eq) and the mixture heated to 60° C. After 90 min (tlc 90:10:1 CH$_2$Cl$_2$/MeOH/NH$_4$OH) it was cooled to room temperature, diluted with aq potassium carbonate solution and extracted with methylene chloride. The organics were dried over magnesium sulphate, filtered and concentrated. The residue was chromatographed (95:5:1 to 90:10:1 CH$_2$Cl$_2$/MeOH/NH$_4$OH) to give the lactam (21 mg, 31%) as a clear oil, (which could be lyophilized from benzene to give a white powder).

$^1$H (400 MHz, CDCl$_3$); δ6.81 (1H, d, J 9.1 Hz, NH), 4.78 (1H, d, J 11.3 Hz, H-13), 4.72 (1H, d, J 4.5 Hz, H-1″), 4.61 (1H, d, J 7.2 Hz, H-1′), 4.30 (1H, d, J 2.9 Hz, H-3), 4.16 (1H, ddd, J 14.4, 10.5, 1.9 Hz, H-11), 4.06 (1H, dq, J 9.5, 6.2 Hz, H-5″), 3.90 (1H, br s, OH), 3.86 (1H, d, 5.5 Hz, H-5), 3.56 (1H, m, H-5′), 3.34 (3H, s, OMe), 3.30 (1H, dd, J 10.2, 7.2 Hz, H-2′), 3.01 (1H, apparent t, J 9.8 Hz, H-4″), 2.66 (1H, d, J 14.4 Hz, H-11), 2.60–2.40 (3H, m, H-2, H-8, H-3′), 2.36 (1H, d, J 15.4 Hz, H-2″ eq), 2.30 (6H, s, NMe$_2$), 2.17 (1H, d, J 10.3

Hz, 4"-OH), 2.13 (1H, d, J 2.0 Hz, 2'-OH), 2.00 (1H, m, H-14), 1.85 (1H, dd, J 15.3, 10.5 Hz, H-7), 1.81 (1H, m, H-4), 1.68 (1H, br d, J 12.5 Hz, H-4'), 1.62 (1H, d, J 15.4 Hz, H-7), 1.54 (1H, dd, J 15.3, 5.0 Hz, H-2" ax), 1.48 (1H, m, H-14), 1.41 (3H, d, J 6.4 Hz, 2-Me), 1.32 (3H, d, J 6.2 Hz, 5"-Me), 1.28–1.18 (13H, m, H-4', Me, Me, 8-Me, 5'-Me), 1.13–1.08 (6H, m, Me, 4-Me) and 0.83 (3H, t, J 7.3 Hz, 3H-15)ppm.

$^{13}C$ (CDCl$_3$); $\delta$178.3, 176.9, 101.9, 94.9, 83.0, 80.8, 77.6, 76.4, 75.8, 74.7, 72.6, 70.5, 69.4, 66.7, 65.5, 49.3, 43.8, 43.5, 42.3, 40.4, 39.8, 36.7, 34.8, 28.7, 26.6, 23.6, 22.7, 21.6, 21.1, 20.3, 17.7, 11.6, 11.3 and 10.8 ppm.

IR (Film) 3465, 3370, 2970, 2940, 1715, 1660, 1535, 1455, 1380, 1210, 1165, 1105, 1080, 1050, 990, 750 cm$^{-1}$.

FAB MS (Li spike) m/z 711 (M$^+$+Li)

EXAMPLE 10

10-Aza-9-deoxo-11-deoxy erythromycin A

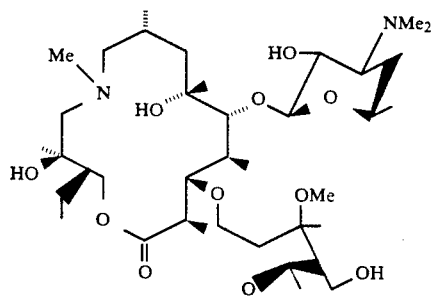

Protected azalide (160 mg, 0.2 mmol) was dissolved in 1:1 THF/MeOH (4.0 mL, 0.05N) and potassium dihydrogen phosphate (933 mg, 35 eq) was added. The mixture was cooled to −20° C. and freshly ground 6% sodium amalgam (1.88 g, 25 eq) was added in one portion. After 45 min an additional 35 eq of potassium dihydrogen phosphate and 25 eq of amalgam were added. After a further 45 min (tlc 95:5:1 CH$_2$Cl$_2$/MeOH/NH$_4$OH) the mixture was decanted into aq.potassium carbonate solution. The amalgam residue was washed several times with ethyl acetate, decanting into the aqueous mixture. This mixture was partitioned and the aqueous reextracted with ethyl acetate. The combined organics were dried over magnesium sulphate, filtered and concentrated. The crude residue was dissolved in methanol (4.0 mL, 0.05N) and formaldehyde (79 μL of a 37% aq.soln, 5 eq) added. Sodium cyanaborohydride (124 mg, 10 eq) was added in one portion. After 90 min a further 5 eq of formaldehyde and 10 eq of borohydride was added and the mixture stirred for a further 12 h (tlc 95:5:1 CH$_2$Cl$_2$/MeOH/NH$_4$OH). Aqueous potassium carbonate was added and the mixture extracted with methylene chloride. The organics were dried over magnesium sulphate, filtered and concentrated. The residue was chromatographed (95:5 CH$_2$Cl$_2$/MeOH; 97.5:2.5:0.5 to 95:5:1 CH$_2$Cl$_2$/MeOH/NH$_4$OH) to give the azalide (80 mg, 58%) as a clear oil, (which could be lyophilized from benzene to give a white powder). $^1$H (400 MHz, CDCl$_3$):$\delta$4.83 (1H, dd, J 10.6, 2.6 Hz, H-13), 4.71 (1H, br d, J 2.7 Hz, H-1"), 4.54 (1H, d, J 7.3 Hz, H-1'), 4.48 (1H, br s, H-3), 4.02 (1H, dq, J 8.7, 6.5 Hz, H-5"), 3.68 (1H, d, J 5.1 Hz, H-5), 3.56 (1H, m, H-5'), 3.30 (3H, s, Ome), 3.27 (1H, dd, J 12.2, 4.8 Hz, H-2'), 3.04 (1H, d, J 3.8 Hz, H-4"), 2.79 (1H, d, J 13.4 Hz, H-11), 2.59 (1H, dq, J 7.3, 2.2 Hz, H-2), 2.52 (1H, m, H-3'), 2.33 (3H, s, —NMe), 2.29 (6H, s, —NMe$_2$), 2.28–2.15 (4H, m, 2H-9, H-11, H-2"), 1.92 (2H, m, H-4, H-8), 1.79 (1H, dd, J 14.2, 4.4 Hz, H-7), 1.65 (1H, br d, J 11.3 Hz, H-4'), 1.58 (1H, dd, J 15.0, 4.8 Hz, H-2"), 1.53 (1H, m, H-14), 1.33 (1H, m, H-14), 1.25 (3H, d, J 6.4 Hz, 5"-Me), 1.23–1.15 (17H, m, H-4, H-7, 2-Me, 6-Me, 12-Me, 5'-Me, 3"-Me), 1.08 (3H, d, J 7.3 Hz, Me), 1.03 (3H, d, J 6.6 Hz, Me) and 0.84 (3H, t, J 7.3 Hz, 3H-15) ppm.

$^{13}$C (CDCl$_3$); 176.6, 103.0, 95.2, 85.4, 81.1, 77.9, 77.3, 74.2, 73.0, 71.5, 70.8, 70.1, 69.3, 66.4, 65.2, 63.2, 49.3, 45.5, 44.1, 43.2, 40.4, 34.8, 29.1, 28.4, 26.4, 25.2, 23.2, 21.6, 21.2, 20.8, 17.7, 12.2, 11.1, 10.1 ppm.

IR (Film); 3460, 2975, 2940, 1730, 1455, 1380, 1180, 1160, 1105, 1045, 750 cm$^{-1}$.

FABMS m/z 705 (M+H)

Analysis calcd. for C$_{36}$H$_{68}$O$_{11}$N$_2$: C, 61.34: H, 9.72: N, 3.97%. Found: C, 61.11: H, 9.81: N, 3.81%.

EXAMPLE 11

10-Acetyl-10-Aza-10-desmethyl-9-deoxo-11-deoxy erythromycin A

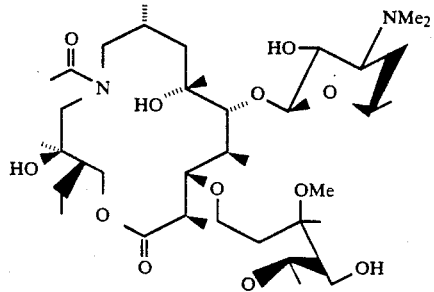

The azalide product of Example 8 (40.0 mg, 49 μmol) was dissolved in pyridine (0.5 mL, 0.1N) at room temperature and acetic anhydride (4.6 μL, 1.0 eq) added. After 4 h (tlc 95:5:1 CH$_2$Cl$_2$/MeOH/NH$_4$OH) the mixture was diluted with aq. potassium carbonate solution and extracted with methylene chloride. The combined organics were dried over magnesium sulphate, filtered and concentrated.

The residue was dissolved in 1:1 THF/MeOH (1.0 mL, 0.04N) and potassium dihydrogen phosphate (166 mg, 30 eq) added. The mixture was cooled to −20° C. and freshly ground 6% sodium amalgam (391 mg, 25 eq) added. After 30 min a further 30 eq of potassium dihydrogen phosphate and 25 eq of sodium amalgam were added. After a further 60 min (tlc 95:5:1 CH$_2$Cl$_2$/MeOH/NH$_4$OH) the mixture was decanted into aqueous potassium carbonate solution. The amalgam residue was washed several times with ethyl acetate and decanted each time into the aqueous mixture. The aqueous was extracted with ethyl acetate and the combined organic extracts dried over magnesium sulphate, filtered and concentrated. The residue was dissolved in chloroform (1.0 mL, 0.04N) and formaldehyde (6.6 μL of 37% aq solution, 2.0 eq) added, followed by formic acid (1.5 μL, 1.0 eq). The mixture was heated to 60° C. After 90 min (tlc 95:5:1 CH$_2$Cl$_2$/MeOH/NH$_4$OH) it was cooled to room temperature and diluted with potassium carbonate solution. The resulting mixture was extracted with methylene chloride, dried over magnesium sulphate, filtered and concentrated. The residue was chromatographed (95:5 CH$_2$Cl$_2$/MeOH to 95:5:1 CH$_2$Cl$_2$/MeOH/NH$_4$OH) to give the amide (11 mg, 31%) as a clear oil. Lyophilization from benzene gave a white powder.

Selected data:

$^1$H (400 MHz; CDCl$_3$) δ4.81 (1H, dd, J 10.2, 3.3 Hz, H-13), 4.71 (1H, br d, J 3.3 Hz, H-1″), 4.64 (1H, d, J 7.3 Hz, H-1′), 4.38 (1H, br t, 2.9 Hz, H-3), 4.31 (1H, br s, OH), 4.22 (1H, br s, OH), 4.04 (1H, dq, J 8.9, 6.5 Hz, H-5″), 3.80 (1H, d, J 3.7 Hz, H-5), 3.68 (1H, d, J 14.3 Hz, H-11), 3.61 (1H, m, H-5′), 3.37–3.23 (6H, m, H-9, H-11, H-2′, OMe), 3.10 (1H, dd, J 13.6, 10.3 Hz, H-9), 3.04 (1H, t, J 7.8 Hz, H-4″), 2.61–2.50 (2H, m, H-2, H-3′), 2.35–2.23 (8H, m, H-2″, 4″-OH, NMe$_2$), 2.15 (1H, br m, H-8), 2.10 (3H, s, Ac), 1.87–1.75 (2H, m, H-4, H-14), 1.67 (1H, br d, J 13.0 Hz, H-4′), 1.61–1.35 (4H, m, 2H-7, H-14, H-2″), 1.30–1.19 (13H, m, H-4′, Me, 2-Me, 5′-Me, 5″-Me), 1.17 (3H, s, Me), 1.15 (3H, s, Me), 1.09 (3H, d, J 7.5 Hz, 4-Me), 1.07 (3H, d, J 6.6 Hz, 8-Me) and 0.86 (3H, t, J 7.4 Hz, 3H-15) ppm.

IR (film); 3450, 2970, 2940, 1730, 1625, 1455, 1375, 1160, 1040 and 745 cm$^{-1}$.

FABMS m/z 734 (M$^+$ +2H)

EXAMPLE 12

4″-Amino-4″-deoxy Azalide

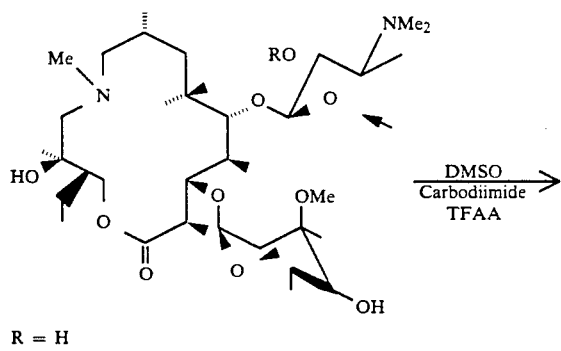

R = H

Ac$_2$O

R = Ac

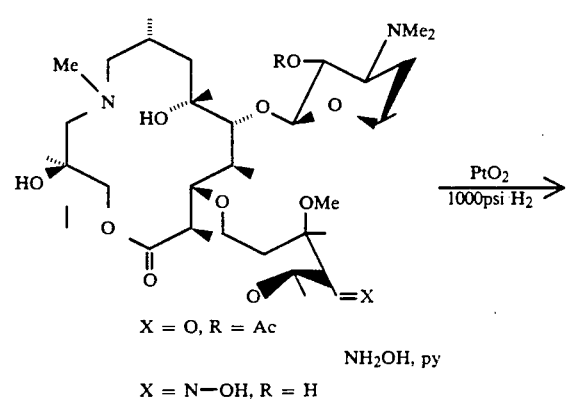

X = O, R = Ac

NH$_2$OH, py

X = N—OH, R = H

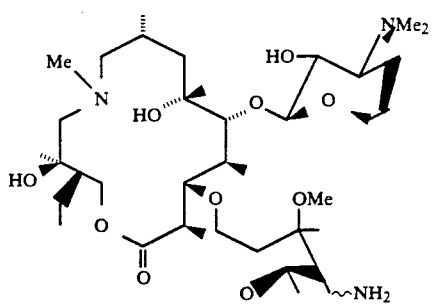

The azalide product of Example 10 (80 mg, 0.11 mmol) was dissolved in ethyl acetate (2.0 mL, 0.06N) at room temperature. Acetic anhydride (16 μL, 1.5 eq) was added. After 12 h (tlc 95:5:1 CH$_2$Cl$_2$/MeOH/N-H$_4$OH) aq potassium carbonate solution was added and the mixture extracted with ethyl acetate. The combined organic extracts were dried over magnesium sulphate, filtered and concentrated to give the acetate derivative (75 mg, 88%) as a white foam that required no further purification.

This acetate (74 mg, 0.10 mmol) was dissolved in methylene chloride (2.0 mL, 0.05N) at room temperature. Methyl sulphoxide (70 μL, 10.0 eq) was added, followed by 1-(3-dimethylaminopropyl)-3-ethyl-carbodiimide hydrochloride (95 mg, 5.0 eq) and finally pyridinium trifluoroacetate (96 mg, 5.0 eq). After 3 h (tlc 95:5:1 CH$_2$Cl$_2$/MeOH/NH$_4$OH) ethyl actetate was added followed by water. The aqueous was adjusted to pH10 with 1.0N sodium hydroxide solution and extracted with ethyl acetate. The organic extracts were dried over magnesium sulphate, filtered and concentrated. Chromatography (95:5 CH$_2$Cl$_2$/MeOH to 95:5:1 CH$_2$Cl$_2$/MeOH/NH$_4$OH) gave the 4″ keto derivative (38 mg, 51%) as a white foam, together with unreacted acetate (18 mg, 24%).

The 4″ keto derivative (40 mg, 54 Mmol) was dissolved in methanol (1.0 mL, 0.05N) at room temperature. Pyridine (43.5 μL, 10 eq) was added, followed by hydroxylamine hydrochloride (18.7 mg, 5 eq). After 24 h (tlc 95:5:1 CH$_2$Cl$_2$/MeOH/NH$_4$OH) the mixture was diluted with ethyl acetate and water and the aqueous adjusted to pH9–10 with 1.0N sodium hydroxide solution. The aqueous was extracted with ethyl acetate and the combined organics dried over magnesium sulphate, filtered and concentrated. The residue was chromatographed (95:5 CH$_2$Cl$_2$/MeOH to 95:5:1 CH$_2$Cl$_2$/MeOH/NH$_4$OH) to give partially purified 4″-oximino derivative (33 mg) as a white foam. This was dissolved in acetic acid (1.0 mL, 0.05N) and platinum oxide (30 mg, ~1 wt eq) added. The mixture was hydrogenated at room temperature and 1000 psi of hydrogen for 72 h. The mixture was filtered through celite, eluting with methylene chloride, and concentrated. The residue was re-concentrated twice from methylene chloride/heptane. Chromatography (95:5:1 CH$_2$Cl$_2$/MeOH/NH$_4$OH) gave the 4″ amino compound (27 mg, 71% over two steps, 1:1 mixture of 4″-stereoisomers) as a white foam. Lyophilization from benzene provided a white powder.

Selected data:

$^1$H (400 MHz; CDCl$_3$) δ4.82 (1H, overlapping dd, J 10.7, 2.7 Hz, H-13), 4.71 (1H, m, H-1″), 4.55 (11/2H, m, H-1′, H-5″(½)), 4.47 (½H, br m, H-3), 4.44 (½H, br m, H-3), 4.00 (½H, dq, J 8.8, 6.4 Hz, H-5″), 3.71 (½H, d, J 5.1 Hz, H-5), 3.68 (½H, d, J 5.1 Hz, H-5), 3.66-3.42 (1H, m, H-5′), 3.34-3.20 (4H, m, H-2′, OMe (singlets at 3.28, 3.27)), 2.81 (½H, d, J 4.3 Hz, H-11), 2.78 (½H, d, J 4.3 Hz, H-11), 2.63-2.50 (2H, m, H-2, H-3′), 2.37-2.14 (13½H, m, 2H-9, H-11, H-2″(½), H-4″, NMe, NMe₂), 2.00 (½H, d, J 15.4 Hz, H-2″), 1.98-1.85 (2H, m, H-4, H-8), 1.78 (1H, m, H-7), 1.64 (1H, m, H-4′), 1.59-1.50 (2H, m, H-14, H-2″), 1.38-1.11 (21H, m, H-7, H-14, H-4′, 3×Me(s), 3×Me(d)), 1.09 (3/2H, d, J 7.3 Hz, Me), 1.08 (3/2H, d, J 7.3 Hz, Me), 1.03 (3/2H, d, J 6.7 Hz, Me), 1.00 (3/2H, d, J 6.6 Hz, Me) and 0.85 (3H, t, J 7.3 Hz, 3H-15) ppm.

EXAMPLE 13

10-Aza-10-(2-cyanoethyl)-10-desmethyl-9-deoxo-11-deoxy erythromycin A

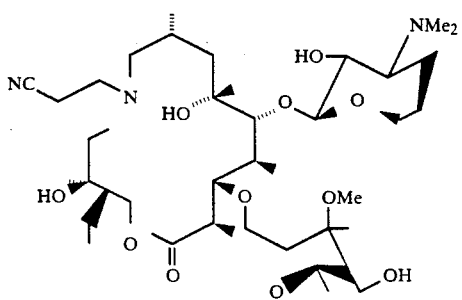

The azalide product of Example 8 (50 mg, 61 μmol) was dissolved in acrylonitrile (0.7 mL, 0.09N) and heated to 60° C. After 12 h (tlc 95:5:1 CH₂Cl₂/MeOH/NH₄OH) the mixture was cooled to room temperature and concentrated. The residue was chromatographed (95:5 CH₂Cl₂/MeOH) to give the cyanoethyl derivative (48 mg, 90%) as a glass. Lyophilization from benzene gave a white powder.

The cyanoethyl derivative (48 mg, 55 μmol) was dissolved in 1:1 THF/MeOH (1.0 mL, 0.06N) and potassium dihydrogen phosphate (263 mg, 35 eq) added.

The mixture was cooled to −20° C. and freshly ground 6% sodium amalgam (529 mg, 25 eq) added. After 30 min a further 35 eq of potassium dihydrogen phosphate and 25 eq of sodium amalgam were added. After a further 30 min (tlc 95:5:1 CH₂Cl₂/MeOH/NH₄OH) the mixture was decanted into aqueous potassium carbonate solution. The amalgam residue was washed several times with ethyl acetate and decanted each time into the aqueous mixture. The aqueous was extracted with ethyl acetate and the combined organic extracts dried over magnesium sulphate, filtered and concentrated. The residue was dissolved in chloroform (1.0 mL, 0.09N) and formaldehyde (9 μL of 37% aq solution, 2.0 eq) added, followed by formic acid (2 μL, 1.0 eq). The mixture was heated to 60° C. After 40 min (tlc 95:5:1 CH₂Cl₂/MeOH/NH₄OH) it was cooled to room temperature and diluted with potassium carbonate solution. The resulting mixture was extracted with methylene chloride, dried over magnesium sulphate, filtered and concentrated. The residue was chromatographed (95:5 CH₂Cl₂/MeOH to 95:5:1 CH₂Cl₂/MeOH/NH₄OH) to give the fully deprotected cyanoethyl azalide (28 mg, 68%) as a clear oil. Lyophilization from benzene gave a white powder.

Selected data:

¹H(400 MHz; CDCl₃) δ4.84 (1H, dd, J 10.5, 2.9 Hz, H-13), 4.74 (1H, apparent t, J 4.0 Hz, H-1″), 4.63 (1H, d, J 7.3 Hz, H-1′), 4.50 (1H, br s, OH), 4.38 (1H, br s, H-3), 4.03 (1H, m, H-5″), 3.80 (1H, d, J 3.3 Hz, H-5), 3.63 (1H, m, H-5′), 3.31 (1H, dd, J 10.3, 7.4 Hz, H-2′), 3.28 (3H, s, OMe), 3.18 (1H, br s, OH), 3.06 (1H, d, J 7.7 Hz, H-4″), 2.99-2.81 (2H, m), 2.69 (1H, d, J 13.9 Hz, H-11), 2.63-2.41 (6H, m), 2.29 (6H, s, NMe₂), 2.26-2.20 (2H, m), 1.80 (2H, m, H-4, H-8), 1.68-1.54 (4H, m, H-7, H-14, H-4′, H-2″), 1.36 (1H, m, H-14), 1.27-1.11 (23H, m), 1.07 (3H, d, J 7.0 0Hz) and 0.86 (3H, t, J 7.4 Hz, 3H-15) ppm.

FABMS (Li spike) m/z 751 (M⁺+Li).

EXAMPLE 14

10-Aza-10-desmethyl-9-deoxo-11-deoxy-10-(3-aminopropyl) erythromycin A

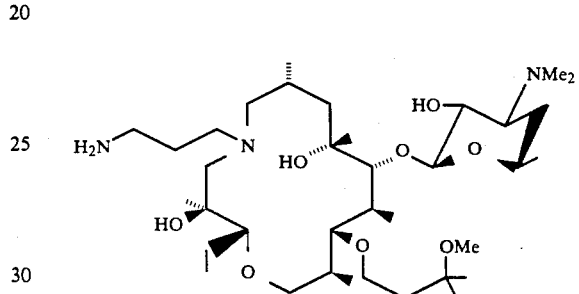

The product of Example 13 (15 mg, 20.2 μmol) was dissolved in methanol (1.0 OmL, 0.02N) and cobalt (II) chloride (9.6 mg, 2.0 eq) added. The mixture was cooled to 0° C. and sodium borohydride (7.6 mg, 10.0 eq) added portionwise. After 30 min (tlc 95:5:1 CH₂Cl₂/MeOH/NH₄OH) the mixture was filtered through celite, eluting with ethyl acetate. The filtrate was diluted with aqueous potassium carbonate solution and partitioned. The aqueous was re-extracted with ethyl acetate and the combined organic extracts dried over magnesium sulphate, filtered and concentrated. The residue was chromatographed (90:10:1 CH₂Cl₂/MeOH/ NH₄OH) to give the aminopropyl derivative (5.5 mg, 36%) as a white foam. Lyophilization from benzene gave a white powder.

Selected data:

¹H (400 MHz; CDCl₃) δ4.79 (1H, dd, J 4.5, 2.7 Hz, H-1″), 4.76 (1H, dd, J 9.2, 3.3 Hz, H-13), 4.58 (1H, d, J 7.3 Hz, H-1′), 4.24 (1H, br t, J 3.4 Hz, H-3), 4.05 (1H, m, H-5″), 3.83 (1H, d, J 3.3 Hz, H-5), 3.62 (1H, m, H-5′), 3.34 (1H, dd, J 10.3, 7.3 Hz, H-2′), 3.28 (3H, s, OMe), 3.04 (1H, d, J 8.5 Hz, H-4″), 2.86-2.73 (2H, m), 2.70-2.49 (6H, m), 2.40 (1H, d, J 13.7 Hz), 2.30 (6H, s, Nme₂), 2.29-2.17 (2H, m), 2.11 (1H, dd, J 12.5, 4.0 Hz), 1.81 (1H, m), 1.75-1.52 (7H, m), 1.36 (1H, m, H-14), 1.30-1.10 (23H, m), 1.06 (3H, d, J 7.1 Hz) and 0.87 (3H, t, J 7.5 Hz, 3H-15)ppm.

EXAMPLE 15

10-Aza-10-desmethyl-9-deoxo-11-deoxy-10,12-O-methylene erythromycin A

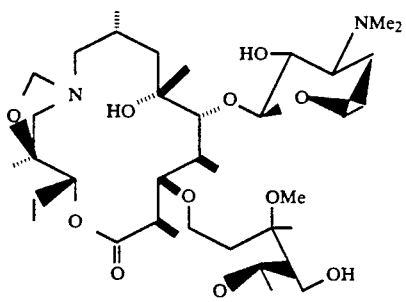

The azalide product from Example 8 (40 mg, 49-mol) was dissolved in 1:1 THF/MeOH (1.0 mL, 0.05N) and cooled to $-20°$ C. Potassium dihydrogen phosphate (200 mg, 30 eq) was added, followed by freshly ground 6% sodium amalgam. After 1 h (tlc 95:5:1 $CH_2Cl_2$/MeOH/$NH_4OH$) the mixture was decanted from the amalgam residue into aq. potassium carbonate solution. The residue was rinsed several times with ethyl acetate. The combined organic/aqueous mixture was partitioned and the organic fraction dried over magnesium sulphate, filtered and concentrated. The residue was chromatographed to give a glass (18.5 mg). This was dissolved in chloroform (1.0 mL, 0.03N) and formaldehyde (8.6-L of 37% aq. solution, 4.0 eq.) added, followed by formic acid (2.0-L, 2.0 eq.). The mixture was heated to 60° C. for 3 h (tlc as above) and then cooled to room temperature and poured into aq. potassium carbonate solution. The mixture was extracted with methylene chloride, dried over sodium sulphate, filtered and concentrated. Chromatography of the residue (95:5:1 $CH_2Cl_2$/MeOH/$NH_4OH$) gave the aminal (11 mg, 32%) as an oil. Lyophilization from benzene gave the material as a white powder.

$^1$H NMR (400 MHz, $CDCl_3$)-5.03 (1H, d, J 2.5 Hz, OCHN), 4.96 (1H, dd, J 11.0, 2.5 Hz, H-13), 4.72 (1H, d, J 7.2 Hz, H-1'), 4.68 (1H, d, J 4.4 Hz, H-1''), 4.45 (1H, d, J 2.6 Hz, H-3), 4.06 (1H, s, 6-OH), 3.96 (1H, dq, J 9.5, 6.2 Hz, H-5''), 3.81 (1H, d, J 0.4 Hz, H-5), 3.57 (1H, m, H-5'), 3.54 (1H, d, J 2.5 Hz, OCHN), 3.34 (3H, s, OMe), 3.31-3.24 (3H, m, 2H-11, H-2'), 2.98 (1H, t, J 9.5 Hz, H-4''), 2.56 (1H, q, J 7.0 Hz, H-2), 2.47 (1H, m, H-3'), 2.40 (1H, d, J 15.4 Hz, H-2''), 2.27 (6H, s, $NMe_2$), 2.20 (1H, d, J 9.9 Hz, 4''-OH), 2.14 (1H, dd, J 12.9, 11.1 Hz, H-9), 2.05 (1H, d, J 8.7 Hz, 2'-OH), 2.03-1.94 (2H, m, H-7, H-9), 1.91 (1H, m, H-4), 1.71 (1H, m, H-8), 1.66-1.49 (3H, m, H-14, H-4', H-2''), 1.36 (1H, m, H-14), 1.23-1.15 (17H, m, H-7, H-4', 2-Me, 5'-Me, 5''-Me, Me, Me), 1.11 (3H, s, Me), 1.06 (3H, d, J 7.3 Hz, 4-Me), 1.04 (3H, d, J 6.6 Hz, 8-Me) and 0.85 (3H, t, J 7.3 Hz, 3H-15)ppm.

$^{13}$C NMR (100 MHz, $CDCl_3$)-176.8, 101.3, 95.3, 85.3, 83.2, 81.0, 78.1, 77.9, 77.3, 74.8, 72.9, 71.1, 69.1, 65.8, 65.0, 60.3, 60.0, 49.3, 43.8, 43.6, 43.0, 40.4, 34.9, 29.9, 28.9, 24.7, 24.1, 23.7, 21.8, 21.2, 20.7, 17.8, 12.2, 10.7 and 10.5 ppm.

IR (film) 3500, 2970, 2930, 1730, 1450, 1375, 1180, 1155, 1105, 1075, 1040, 990 and 750 $cm^{-1}$.

FABMS (Li spike) m/z 703 ($M^+ +1$), 709 ($M^+ +Li$).

Analysis calcd. for $C_{36}H_{66}O_{11}N_2$: C, 61.54; H, 9.40; N, 3.99%. Found: C, 61.26; H, 9.69; N, 3.92%.

EXAMPLE 16

10-Aza-10-desmethyl-9-deoxo-11-deoxy erythromycin A

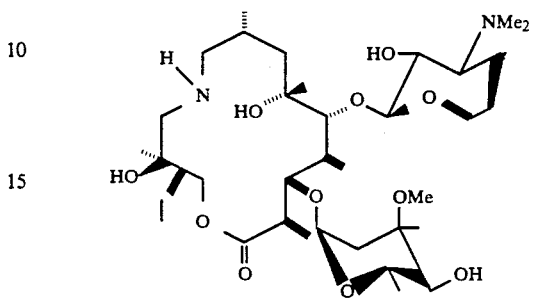

The animal product from Example 15 (35 mg, 50-mol) was dissolved in 3:1:1 AcOH/THF/$H_2O$ (1.0 mL, 0.05N) and ethanolamine hydrochloride (24 mg, 5 eq) added. After 16 h the mixture was basified with aq.$K_2CO_3$ and extracted with $CH_2Cl_2$, dried over $MgSO_4$, filtered and concentrated. The residue, consisting of a mixture of aminal and the secondary amine, was re-subjected to the reaction conditions for a further 16 h and once again extractively isolated. A third iteration was carried out. The resulting residue was chromatographed (95:5:1 to 90:10:1 $CH_2Cl_2$/MeOH/$NH_4OH$) to give the secondary amine (9 mg, 26%) as an oil. Lyophilization from benzene produced a white powder.

Selected data:

$^1$H NMR (400 MHz, $CDCl_3$)-4.95 (1H, dd, J 11.0, 1.2 Hz, H-13), 4.77 (1H, d, J 7.2 Hz, H-1''), 4.65 (1H, d, J 2.3 Hz, H-3), 4.52 (1H, d, J 4.8 Hz, H-1'), 3.98-3.90 (2H, m, H-5, H-5''), 3.59 (1H, m, H-5'), 3.35-3.20 (6H, m, including 3.33 (s) OMe), 3.05 (1H, t, J 9.4 Hz, H-4''), 3.02 (1H, d, J 12.4 Hz, H-11), 2.55-2.47 (2H, m, H-2, H-3'), 2.45 (1H, t, J 10.8 Hz), 2.36-2.23 (9H, m, including 2.27 (s) $NMe_2$), 2.18 (1H, d, J (9.6 Hz), 1.98 (1H, m, H-8), 1.82 (1H, m, H-4), 1.68-1.50 (4H, m, H-7, H-14, H-4', H-2''), 1.37 (1H, m, H-14), 1.29-1.07 (26H, m) and 0.86 (3H, t, J 7.3 Hz, 3H-15)ppm.

FABMS (Li spike) m/z 691 ($M^+$), 698 ($M^+ +Li$).

As antibiotics, the compounds of formula (I) can be administered in such oral dosage forms as tablets, capsules, pills, powders, granules, elixirs, tinctures, suspensions, syrups and emulsions. Likewise, they may also be administered in intravenous, intraperitoneal, subcutaneous or intramuscular form, all using forms well known to those of ordinary skill in the pharmaceutical arts. In general, the preferred form of administration is oral. An effective but non-toxic amount of the compound can be employed as a mammalian antibiotic.

The dosage regimen utilizing the compounds of formula (I) is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Dosages of the compounds of formula (I), when used for the indicated effects, will range between about 0.2 mg per kg of body weight per day (mg/kg/day) to about 120 mg/kg/day and preferably 4–50 mg/kg/day. Advantageously, the compound may be administered in a single daily dose, or the total daily dosage may be administered in divided doses of two, three or four times daily.

Furthermore, the compounds of formula (I) can be administered in topical, otic or ophthalmic form via use of suitable vehicles.

In the methods of using the compounds (I), they can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups, and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol, and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes, and the like. Disintegrators include, without limitation, starch, methyl cellulose, agar, bentonite, xanthan gum, and the like.

The compounds of formula (I) can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of formula (I) may also be coupled with soluble polymers as targetable drug carriers. Such polymers can include polyvinylpyrrolidone, pyran copolymer, polyhydroxypropylmethacrylamide phenyl, polyhydroxyethylaspartamide-phenol, or polyethyleneoxide-polylysine substituted with palmitoyl residues. Furthermore, the compound of formula (I) may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross-linked or amphipathic block copolymers of hydrogels.

EXAMPLE 17

The antibacterial activity assay employs a liquid turbidimetric microtiter method for the determination of the minimum inhibitory concentration (MIC) in broth media. The MIC endpoint in mcg/ml is defined as the lowest concentration of test compound that completely inhibits the growth (absence of turbidity) of bacteria. The MIC is generally not an absolute value but rather a concentration range that falls within a two-fold dilution limit. Generally twelve two-fold dilutions of the test compound are employed with the initial concentration set at 128 mcg/ml. A representative list of microorganisms sensitive to antibiotics of the same class as Formula (I) is given below.

| Microorganism | Strain |
| --- | --- |
| Enterococcus faecalis | MB 5407 |
| Enterococcus faecium | MB 5416 |
| Streptococcus agalactiae | CL 1343 |
| Staphylococcus aureus | MB 2865 |
| Staphylococcus epidermidis | MB 5414 |
| Staphylococcus haemolyticus | MB 5412 |
| Streptococcus pneumoniae | CL 2883 |
| Streptococcus pyogenes | MB 2874 |
| Streptococcus pyogenes | MB 54061 |
| Steptococcus viridans | CL 2943 |
| Escherichia coli | MB 2884 |
| Escherichia coli | MB 4926 |
| Klebsiella pneumoniae | MB 4005 |
| Pseudomonas stutzeri | MB 1231 |

The compounds of formula (I) are useful as antibacterial agents both in vitro and in vivo, and their spectrum of activity is similar to that of erythromycin A. Consequently, they can be used for the same purposes, and, in the same manner as erythromycin A. In general, the antibacterial compounds of formula II and salts thereof, exhibit in vitro activity against a variety of Gram-positive microorganisms, e.g. *Streptococcus pyogenes*, and against certain Gram-negative microorganisms such as those of spherical or ellipsoidal shape (cocci). Their activity is readily demonstrated by in vitro tests against various micro-organisms. Their in vitro activity renders them useful for topical application; for sterilization purposes, e.g., sick-room utensils; and as industrial antimicrobials, for example, in water treatment, slime control, and preservation of paint and wood. The extrapolation of such in vitro tests to support for such utilities for macrolide compounds is taught in U.S. Pat. No. 4,518,590.

While the invention has been described, exemplified and illustrated in reference to certain preferred embodiments thereof, those skilled in the art will appreciate that various changes, modifications and substitutions can be made therein without departing from the spirit and scope of the invention.

It is intended, therefore, that the invention be limited only by the scope of the claims which follow and that such claims be interpreted as broadly as is reasonable.

What is claimed is:

1. A compound of the formula:

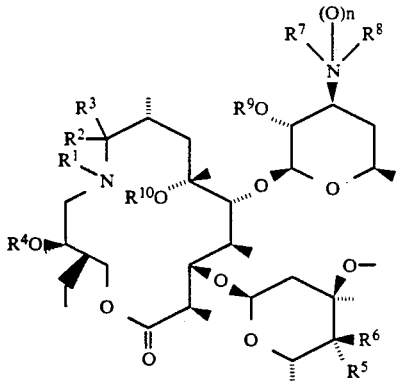

and the pharmaceutically acceptable salts, esters and metal complexes thereof, wherein $R^1$ is
hydrogen,
$C_1-C_{10}$ alkoxycarbonyl,
arylsulfonyl,
$C_1-C_{10}$ alkylsulfonyl, unsubstituted or substituted $C_1-C_{10}$ alkylcarbonyl wherein said substituents are selected from the group consisting of
halogen,
cyano,
aryl,
5 or 6 membered heterocyclic rings; having one heterocyclic atom where said heterocyclic atom is
O or N,
indole,
isoindole,
$C_1-C_{10}$ alkoxycarbonyl,
$C_1-C_{10}$ alkoxy,
hydroxy,
mercapto,
$C_1-C_{10}$ alkylthio,
amino,
mono- or di-$C_1-C_{10}$ alkyl amino,
or $C_1-C_{10}$ alkylcarbonylamino;
$R^2$ and $R^3$ are hydrogen;
$R^2$ and $R^3$ are together oxo or thiono;
$R^4$ is hydrogen, $C_1-C_{10}$ alkyl or $C_1-C_{10}$ alkylcarbonyl;
$R^1$ and $R^4$ together are $C_1-C_3$ alkylidene which can be substituted by oxo;
$R^5$ and $R^6$ independently are
hydrogen,
$C_1-C_{10}$ alkoxy,
$C_1-C_{10}$ alkylcarbonyloxy or $NHR^{11}$ where $R^{11}$ is hydrogen, hydroxy, carbonyl, $C_1-C_{10}$ alkoxycarbonyl, arylsulfonyl, $C_1-C_{10}$ alkysulfonyl, unsubstituted or substituted $C_1-C_{10}$ alkyl or unsubstituted or substituted $C_1-C_{10}$ alkylcarbonyl where said substituents are selected from the group consisting of halogen, cyano,
aryl,
indole,
isoindole,
$C_1-C_{10}$ alkoxycarbonyl,
$C_1-C_{10}$ alkoxy,
hydroxy,
mercapto,
$C_1-C_{10}$ alkylthio,
amino,
mono- or di-$C_1-C_{10}$ alkylamino, $C_1-C_{10}$ alkylcarbonylamino or 5 or 6 membered heterocyclic rings having 1 heteroatom where said heteroatom is N or O;
$R^5$ and $R^6$ together are oxo or oximino;
$R^7$ and $R^8$ are independently hydrogen, $C_1-C_{10}$ alkyl,
$C_1-C_{10}$ alkylcarbonyl or arylsulfonyl;
$R^9$ is hydrogen, or $C_1-C_{10}$ alkylcarbonyl;
$R^{10}$ is hydrogen or $C_1-C_{10}$ alkyl;
$R^1$ and $R^{10}$ together are $C_1-C_3$ alkylidene which can be substituted by oxo; and
m and n are independently integers of from 0 to 1.

2. A compound of the formula:

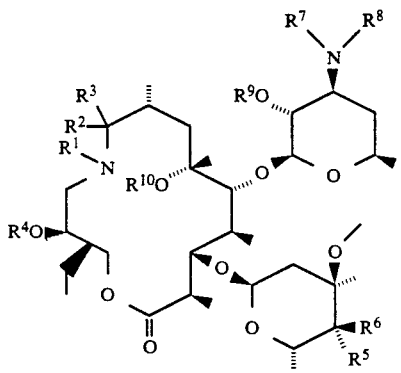

and the pharmaceutically acceptable salts, esters and metal complexes thereof, wherein
$R^1$ is hydrogen,
$C_1-C_{10}$ alkylcarbonyl or unsubstituted or substituted $C_1-C_{10}$ alkyl where said substituent is amino or cyano;
$R^2$ and $R^3$ are hydrogen;
$R^2$ and $R^3$ together are oxo;
$R^4$ is hydrogen or C1-C10 alkylcarbonyl;
$R^5$ and $R^6$ are independently hydrogen, hydroxy or amino;
$R^5$ and $R^6$ together are oxo or oximino;
$R^7$ and $R^8$ are independently hydrogen, $C_1-C_{10}$ alkyl or phenylsulfonyl;
$R^9$ is hydrogen, or C1-C10 alkylcarbonyl, and
$R^{10}$ is hydrogen.

3. The compound as claimed in claim 1, having the structural formula:

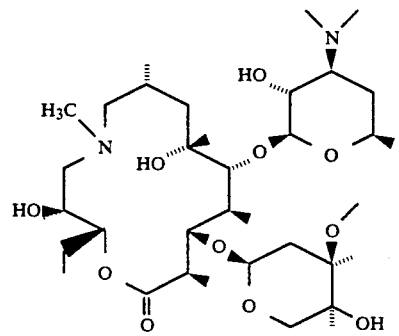

4. The compound as claimed in claim 1, having the structural formula:

5. The compound is claimed in claim 1, having the structural formula

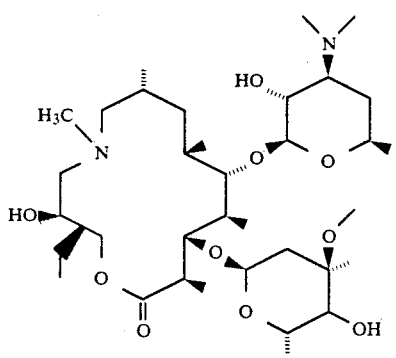

6. The compound as claimed in claim 1, having the structural formula:

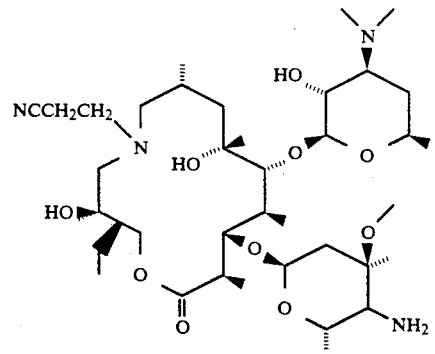

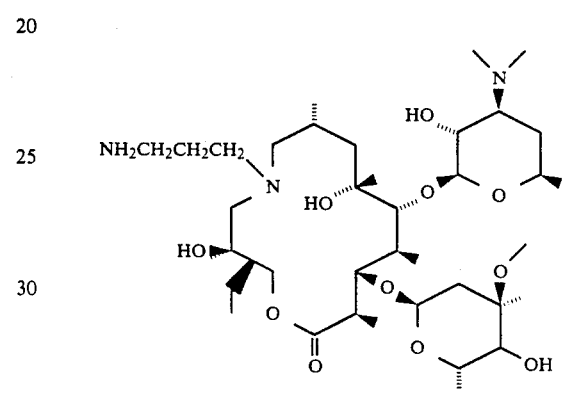

7. A pharmaceutical composition, comprising a pharmaceutically acceptable carrier and an antibiotically effective amount of a compound as claimed in claim 1.

8. A method of treating a bacterial infection in a mammal in need thereof comprising the step of administering to said mammal a pharmacologically effective amount of a compound as claimed in claim 1.

* * * * *